United States Patent [19]
Shofner et al.

[11] Patent Number: 5,560,194
[45] Date of Patent: Oct. 1, 1996

[54] METHOD FOR OPTIMALLY CONTROLLING FIBER PROCESSING MACHINES

[75] Inventors: Frederick M. Shofner, Knoxville, Tenn.; Manfred Frey, Seuzach; Richard Furter, Zug, both of Switzerland; Youe-T Chu; Anja C. Schleth, both of Knoxville, Tenn.

[73] Assignee: Zellweger Uster, Inc., Knoxville, Tenn.

[21] Appl. No.: 341,292

[22] Filed: Nov. 15, 1994

Related U.S. Application Data

[63] Continuation of Ser. No. 999,212, Dec. 31, 1992, abandoned.

[51] Int. Cl.⁶ ............................. G06F 15/46; D01H 13/26
[52] U.S. Cl. .................................................. 57/264; 364/150
[58] Field of Search ...................... 57/264, 265; 364/150, 364/151, 470, 578

[56] References Cited

U.S. PATENT DOCUMENTS

| | | | |
|---|---|---|---|
| 3,953,961 | 5/1976 | Harrap et al. | 57/264 X |
| 4,408,447 | 10/1983 | Sloopensky et al. | 57/264 X |
| 4,899,286 | 2/1990 | Colli et al. | 57/264 X |
| 5,119,308 | 6/1992 | Samoto | 57/265 X |
| 5,146,739 | 9/1992 | Lorenz | 57/264 |
| 5,161,111 | 11/1992 | Oehler et al. | 57/264 X |

*Primary Examiner*—William Stryjewski
*Attorney, Agent, or Firm*—Luedeka, Neely & Graham

[57] ABSTRACT

The invention relates to the field of control of textile machinery which enables optimal control of fiber processing machinery to achieve a target operating point. The method optimizes the processing of fibers by determining a machinery model which simulates a fiber processing machine and introduces to the model different parameters related to the machinery and the input fibers to create optimized settings for the parameters of the machinery and the input fibers for the desired output. These optimal settings are introduced to the machinery and the inputted fibers to process the fibers to achieve the desired output.

16 Claims, 29 Drawing Sheets

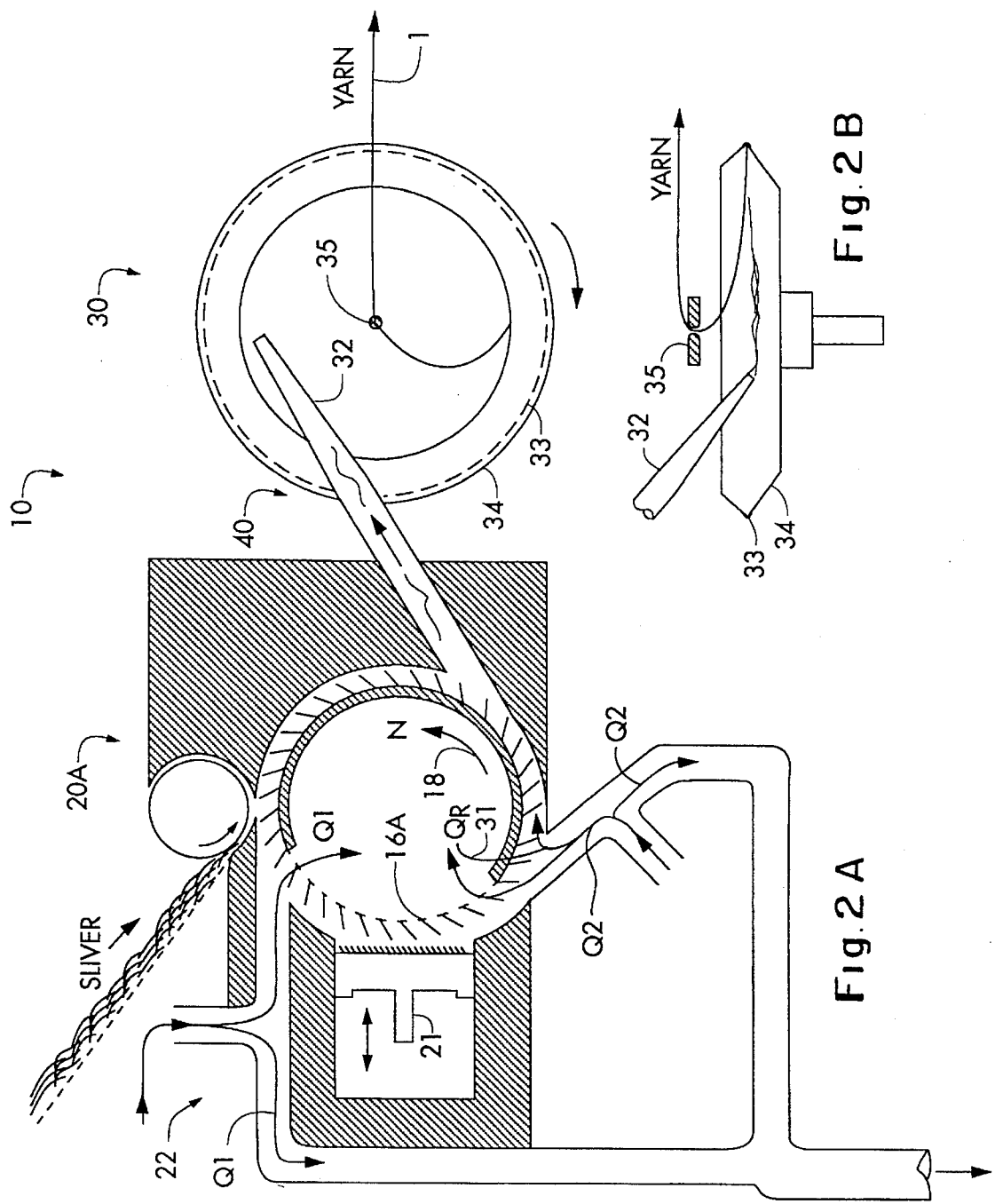

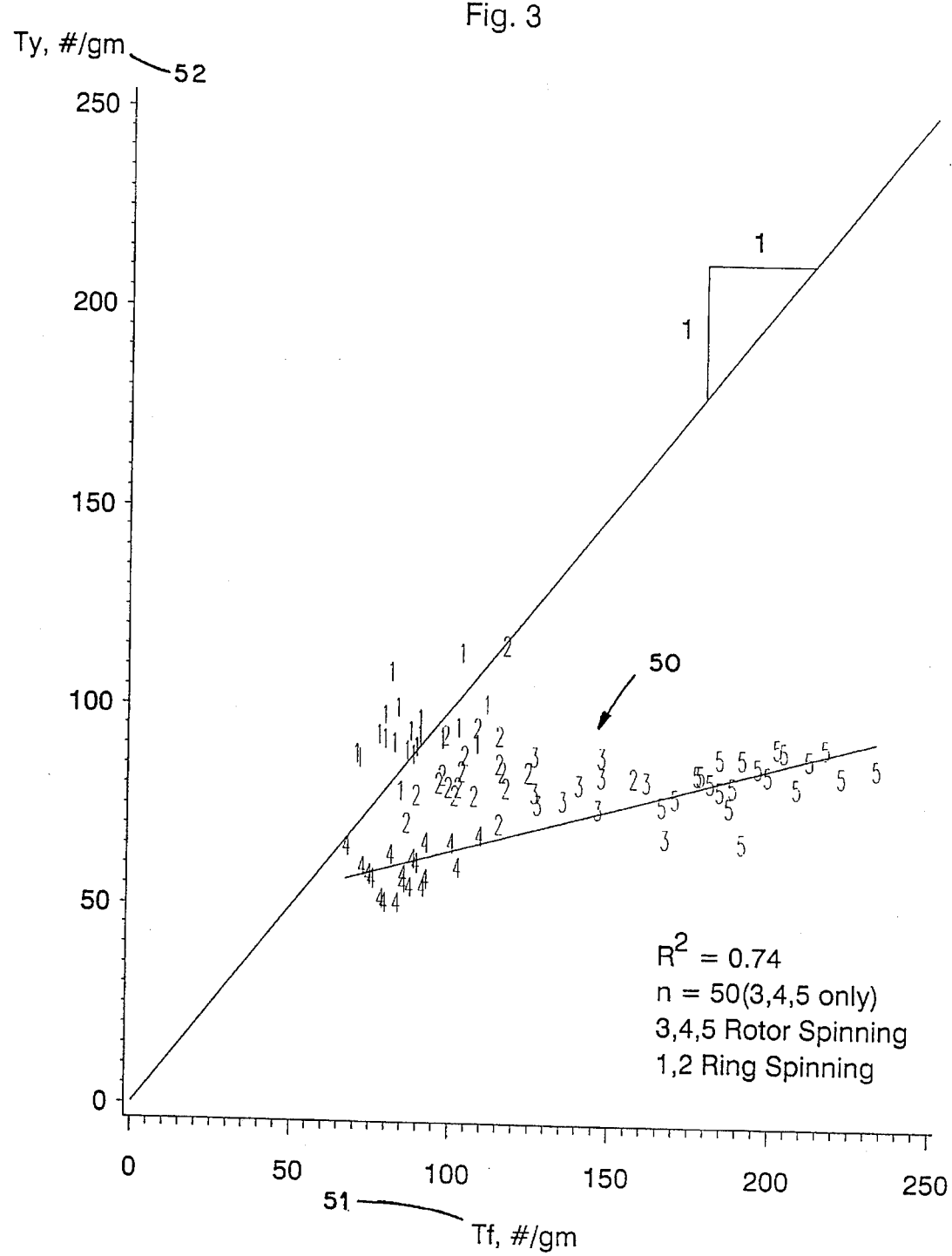

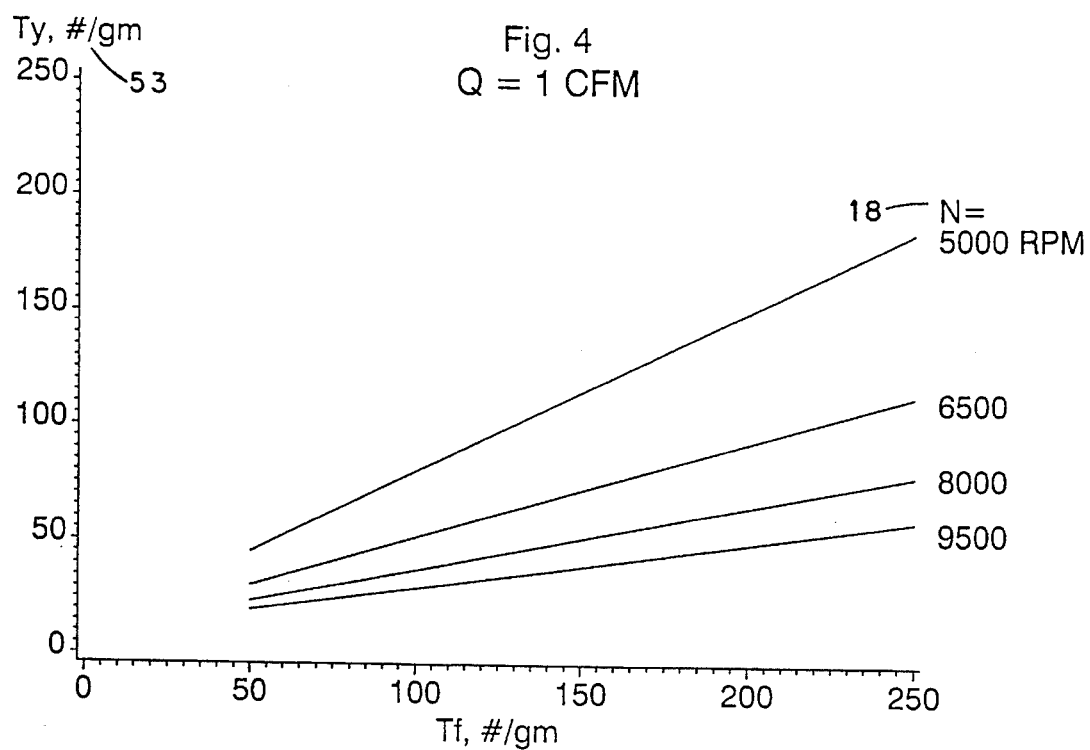
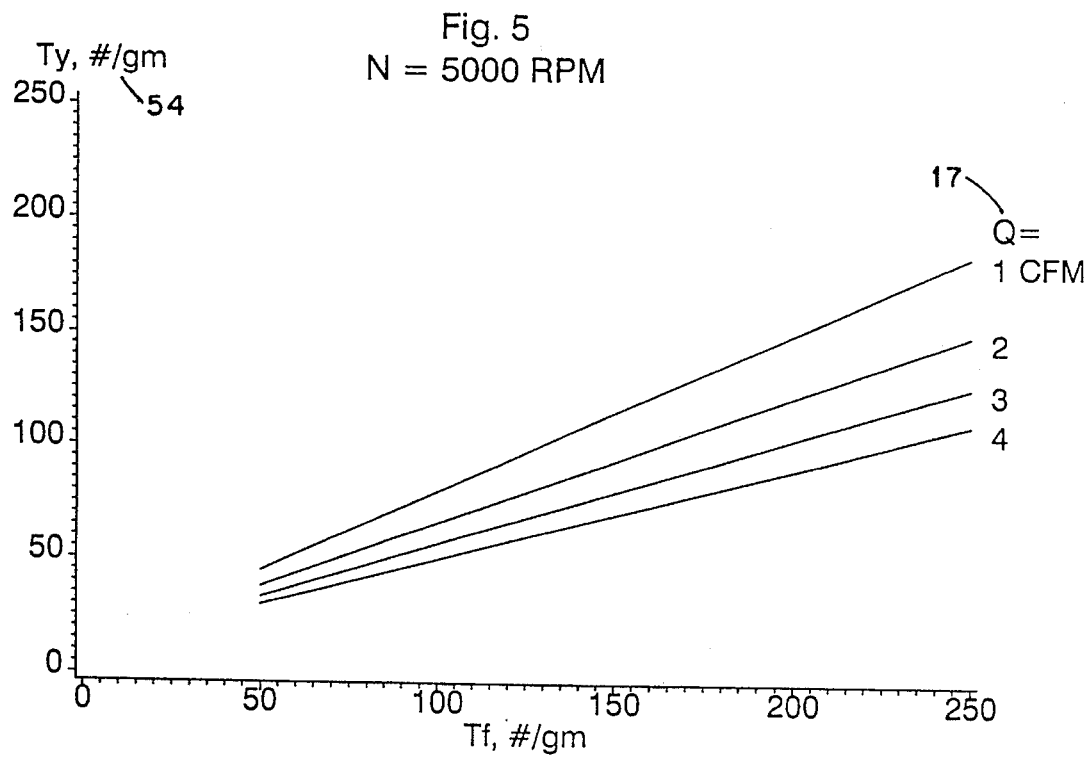

Machinery Characteristics
Tf = 50/gm, SFf = 7%

Q, CFM □ 1   × 2   ○ 3   ● 4

Machinery Characteristics
Tf = 150/gm, SFf = 7%

Q, CFM ☐ 1  × 2  ○ 3  ● 4

Machinery Characteristics
Tf = 250/gm, SFf = 7%

Q, CFM □ 1   × 2   ○ 3   ● 4

Machinery Characteristics
Tf = 50/gm, SFf = 13%

Q, CFM □ 1  ✶ 2  ○ 3  ● 4

Machinery Characteristics
Tf = 150/gm, SFf = 13%
Q, CFM □ 1   × 2   ○ 3   ● 4
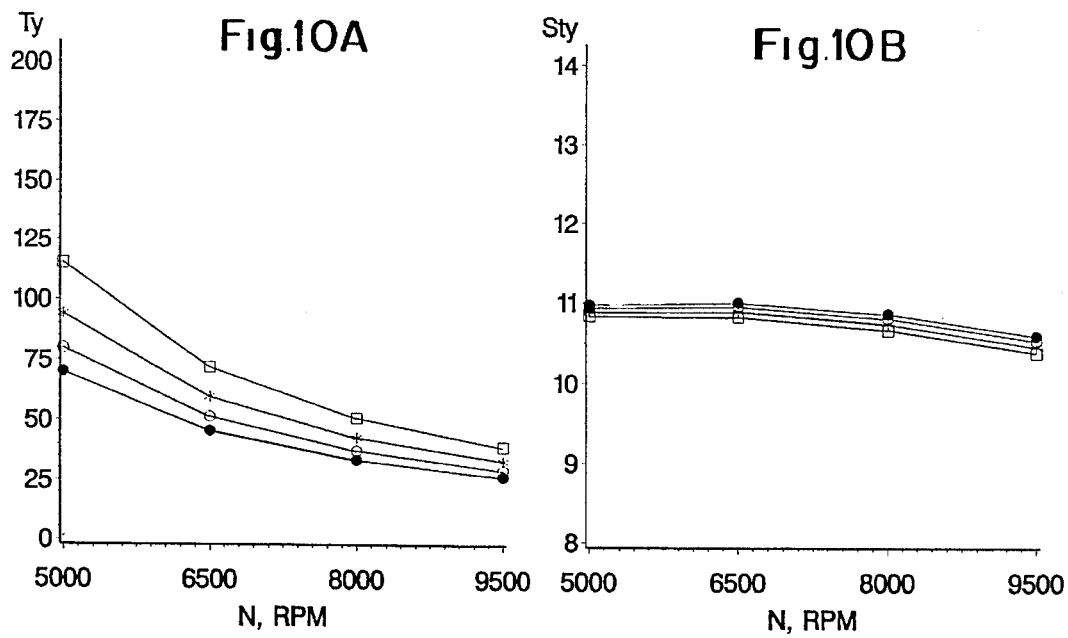
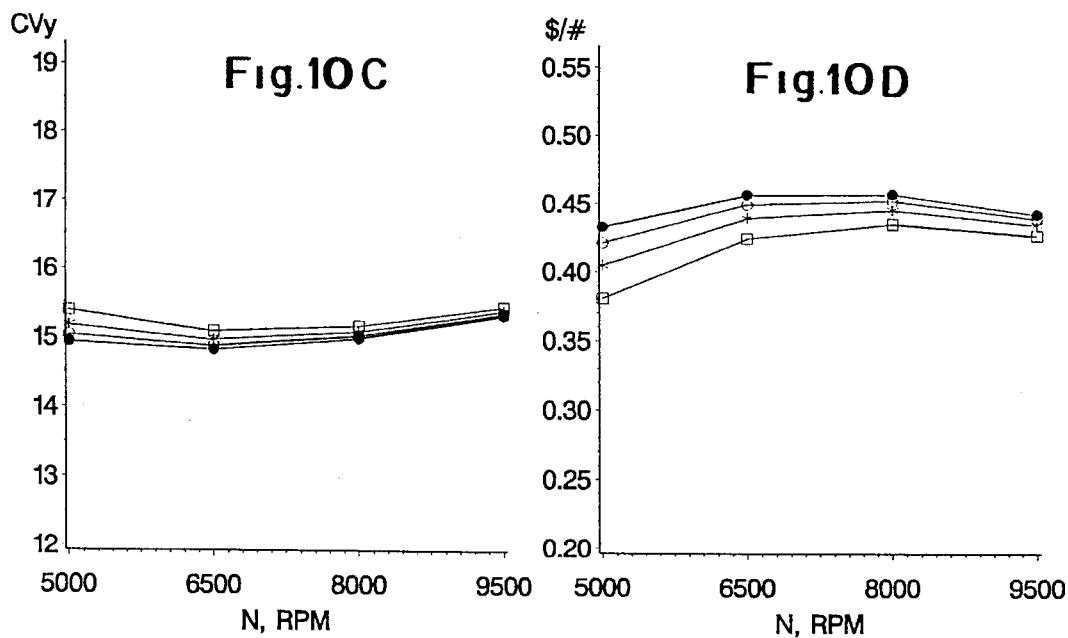

Machinery Characteristics
Tf = 250/gm, SFf = 13%

Q, CFM ☐ 1   × 2   ○ 3   ● 4

Machinery Characteristics
Tf = 50/gm, SFf = 19%

Q, CFM □ 1  × 2  ○ 3  ● 4

Machinery Characteristics
Tf = 150/gm, SFf = 19%

Machinery Characteristics
Tf = 250/gm, SFf = 19%

Q, CFM ☐ 1  ✕ 2  ○ 3  ● 4

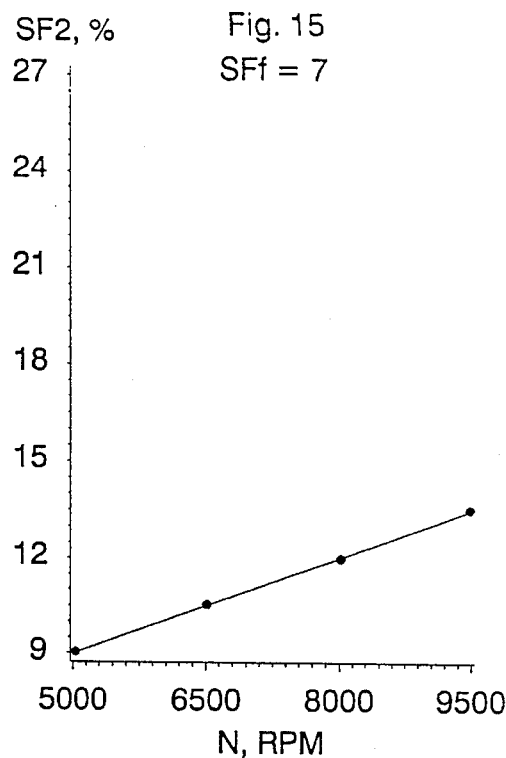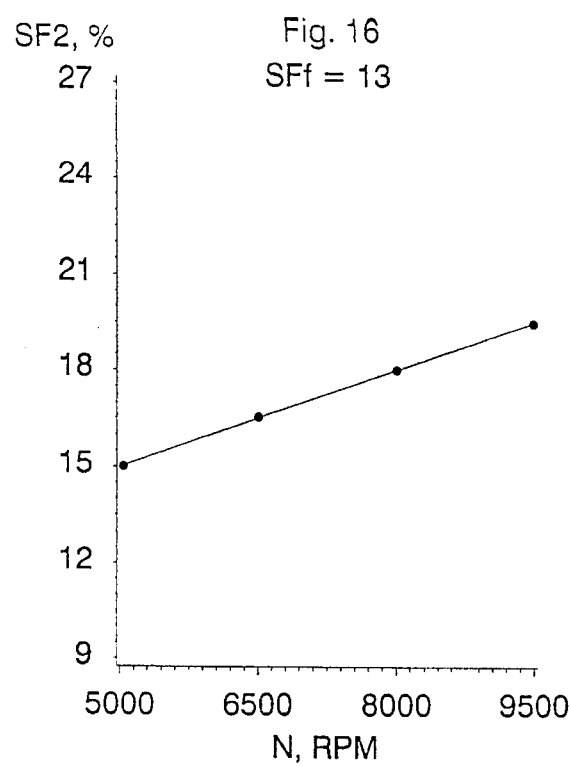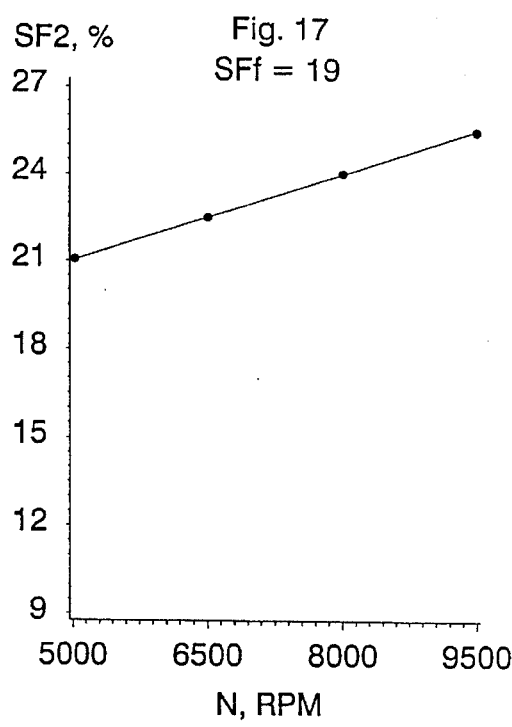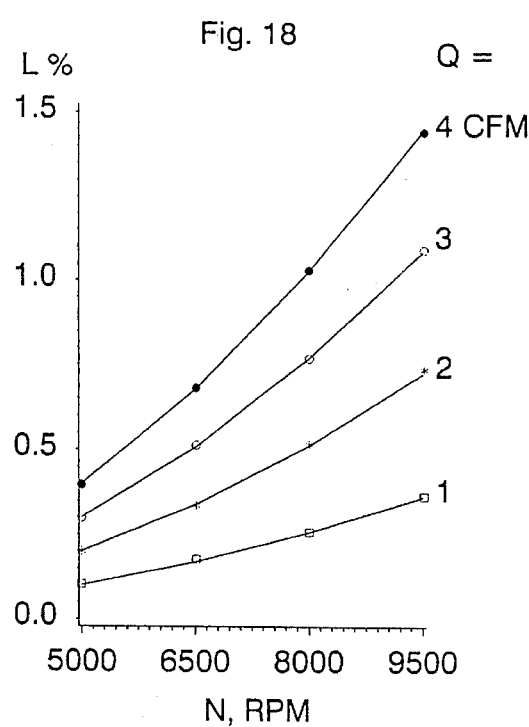

Fig. 25

SPINNING SYSTEMS FOR CARDED COTTON YARNS

Ring Spinning

1. Bale Opening (2)
2. Cleaning (2)
3. Mixing/Blending (2)
4. Carding (32)
5. Breaker Drawing (8)
6. Finish Drawing (8)
7. Roving Positions (1,400)
8. Ring Spinning (42,000)

Rotor Spinning

1. Bale Opening (2)
2. Cleaning (2)
3. Mixing/Blending (2)
4. Carding (32)
5. Breaker Drawing (8)
6. Finish Drawing (8)
7. Rotor Spinning (26,000)

Fig. 26 MAIN QUALITY PARAMETERS

| Fiber | Machinery | Yarn | Fabric |
|---|---|---|---|
| tenacity or strength | machine elements | count | appearance |
| elongation | internal settings | tenacity or strength | abrasion resistance |
| length | stability (wear) | elongation | strength |
| short fiber content | environmental conditions | evenness | uniformity |
| fineness | production rate, efficiencies | fineness | hand |
| maturity | personnel | hairiness | dye performance |
| color | | twist | air permeability |
| various imperfections such as trash, neps, bark, grass, etc | | various imperfections such as trash, neps, thick and thin places | |
| moisture content | | | |
| sticky points | | | |
| sugar content | | | |

Fig. 27 PROCESS AND PROFIT CHARACTERISTICS, M AND P

Process (Fibers and Machinery) (2a)

Input or intermediate fiber parameters: (2b)

$T_F$ = Trash Counts/gm in the input fiber $SF_F$ = Short Fiber Content % in the Input Fiber $T2$ = Trash Counts/gm at Stage 2

$SF2$ = Short Fiber Content % at Stage 2

Variable machinery settings: (2c)

N = Rotational Speed, RPM
Q = Trash Air Flow Rate, CFM
L = Fiber Loss Between Input and Stage 2

Output (yarn) properties: (2d)

$T_y$ = Trash Counts/gm in the Yarn
$St_y$ = Strength (tenacity) of the Yarn
$CV_y$ = Yarn Evenness, Coefficient of Variation Gross Profit P = Yarn Selling Price − Cost of Goods Manufactured (2e)

$$T_y = T2 = 10 + \frac{7 \times 10^7 T_F}{N^2 (Q+3)} \quad \#/gm$$

$$SF_y = SF2 = S_F + (10^{-3} N) - 3 \quad \%$$

$$CV_y = \frac{8.5 + T2 + \frac{SF2}{100} + 2\exp[-(\frac{N}{5000})^2]}{3} \quad \%$$

$$St_y = 14 + \frac{30}{T2 + 10} - \frac{(SF2 - 7)}{3} - 2\exp[-(\frac{N}{5000})^2] \quad gm/tex$$

$$L = 4 \times 10^{-9} QN^2$$

Gross Profit

$$P = \frac{0.35 - (T_y - 15)}{1000} - \frac{(CV_y - 12)}{150}$$

$$+ (-2 + 0.325 \, St_y - 0.0125 \, St_y^2) \quad \$/\#$$

$$- 0.01 L(\%) + C$$

See Equation 15 for ranges of validity.
C is a raw materials cost adjustment factor.

| $SF_F/T_F$ | 50 | 150 | 250 / gm |
|---|---|---|---|
| 7% | 0 | 0.05 | 0.10 |
| C = 13 | 0.05 | 0.10 | 0.15 |
| 19 | 0.10 | 0.15 | 0.20 |

Fig. 28

α - Model for Initial Target Operating Point

X: (N = 7250 RPM, Q = 2.5 CFM)
F: (Tf = 150/gm, SFf = 13%)

| Variables | Cj (without noise) | | | Cj (with 10% noise in fiber measurements) ( 5% noise in yarn measurements) ( 0% noise in machinery measurements) | | |
|---|---|---|---|---|---|---|
| | Ty | STy | CVy | Ty | STy | CVy |
| CONSTANT | 45.760769 | 10.875531 | 14.952677 | 50.210464 | 10.543185 | 15.409369 |
| ΔN | -0.000275 | -0.000009 | 0.000004 | -0.000247 | -0.000009 | 0.000004 |
| ΔQ | -0.183913 | 0.005286 | -0.005629 | -0.176553 | 0.006584 | -0.011652 |
| ΔTf | 0.006563 | -0.000243 | 0.000201 | 0.005694 | -0.000386 | 0.000293 |
| ΔSFf | 0.000000 | -0.030650 | 0.022293 | 0.003107 | -0.030463 | 0.020446 |
| ΔNΔN | 0.000000 | -0.000000 | 0.000000 | 0.000000 | -0.000000 | -0.000000 |
| ΔQΔQ | 0.033942 | -0.000412 | 0.001041 | 0.031774 | 0.002611 | -0.002438 |
| ΔTfΔTf | -0.000000 | 0.000001 | -0.000000 | -0.000007 | 0.000001 | -0.000000 |
| ΔSFfΔSFf | 0.000000 | 0.000000 | 0.000000 | -0.000664 | 0.001187 | -0.000652 |
| ΔNΔQ | 0.000051 | 0.000000 | 0.000002 | 0.000050 | -0.000004 | -0.000001 |
| ΔNΔTf | -0.000002 | -0.000000 | -0.000000 | -0.000001 | -0.000000 | -0.000000 |
| ΔNΔSFf | 0.000000 | 0.000000 | -0.000000 | -0.000001 | 0.000001 | 0.000000 |
| ΔQΔTf | -0.001226 | -0.000006 | -0.000038 | -0.001163 | -0.000091 | -0.000078 |
| ΔQΔSFf | 0.000000 | 0.000000 | -0.000000 | -0.000388 | -0.000584 | 0.000248 |
| ΔTfΔSFf | 0.000000 | 0.000000 | 0.000000 | 0.000021 | -0.000008 | 0.000009 |

Fig. 29

Tf = 150/gm, SFf = 13%

| | | | M, without noise | | α - M | | |
|---|---|---|---|---|---|---|---|
| N<br>KRPM | Q<br>CFM | Ty<br>#/gm | STy<br>gm/tex | CVy<br>% | Ty-Ty | STy-STy | CVy-CVy |
| 5.0 | 1 | 115.0 | 10.8 | 15.4 | 0.2 | -0.5 | -0.1 |
| 6.5 | 1 | 72.1 | 10.8 | 15.1 | 8.4 | -0.3 | 0.4 |
| 8.0 | 1 | 51.0 | 10.7 | 15.2 | 5.3 | -0.2 | 0.5 |
| 9.5 | 1 | 39.1 | 10.4 | 15.4 | 3.4 | -0.2 | 0.3 |
| 5.0 | 2 | 94.0 | 10.9 | 15.2 | 3.5 | -0.4 | 0.1 |
| 6.5 | 2 | 59.7 | 10.9 | 15.0 | 6.9 | -0.3 | 0.5 |
| 8.0 | 2 | 42.8 | 10.7 | 15.1 | 3.3 | -0.3 | 0.5 |
| 9.5 | 2 | 33.3 | 10.5 | 15.4 | 2.8 | -0.3 | 0.2 |
| 5.0 | 3 | 80.0 | 10.9 | 15.0 | 3.0 | -0.3 | 0.1 |
| 6.5 | 3 | 51.4 | 11.0 | 14.9 | 4.4 | -0.3 | 0.4 |
| 8.0 | 3 | 37.3 | 10.8 | 15.0 | 1.8 | -0.3 | 0.3 |
| 9.5 | 3 | 29.4 | 10.5 | 15.3 | 3.4 | -0.4 | 0.0 |
| 5.0 | 4 | 70.0 | 11.0 | 14.9 | 1.7 | -0.1 | 0.0 |
| 6.5 | 4 | 45.5 | 11.0 | 14.8 | 2.8 | -0.2 | 0.2 |
| 8.0 | 4 | 33.4 | 10.9 | 15.0 | 1.9 | -0.3 | 0.1 |
| 9.5 | 4 | 26.6 | 10.6 | 15.3 | 6.1 | -0.5 | -0.3 |

Fig. 30

| $R^2$ | α Model without Noise | α Model with Noise |
|---|---|---|
| Ty | 0.9847 | 0.9630 |
| STy | 0.9999 | 0.8586 |
| CVy | 0.9992 | 0.7942 |

Fig. 31

Maximum Profit Contours

Input Fiber: Tf = 150/gm, SFf = 13%

Optimum Conditions:

|  | α Model | M |
|---|---|---|
| Max. Profit ($/#) | 0.443 | 0.459 |
| Ty (/gm) | 43.8 | 38.1 |
| STy (gm/tex) | 10.8 | 11.0 |
| CVy (%) | 15.0 | 14.9 |
| Q (CFM) | 4.0 | 4.0 |
| N (RPM) | 6900 | 7300 |

AIR (CFM)

```
1.0  00000000000000000099988877777766666666666666777
1.2  00000000000000000999888877777666666666666666777
1.4  0000000000000009988887777666666666666666666777
1.6  000000000000099988877776666666666666666666677777
1.8  00000000000999888777766666655555555556666667777
2.0  000000000999888777766666555555555555555566666777
2.2  00000009998877776666555555555555555555566666777
2.4  0000099988777666655555554444444445555556666777
2.6  0009998877766665555544444444444444455556666778
2.8  099988877766655554444444444444444444445555666778
3.0  988877666555544444333333333333344444555666778
3.2  877766655544443333333333333333333344445555566778
3.4  7766555444433333322222222222333333344455566778
3.6  66555444333322222222222222222222233333444556677 8
3.8  554443333222221111111111111122222333444556667 8
4.0  4433322222111111111$111111111112222333445556678

55555555556666666666777777777788888888889 99999
     012345678901234567890123456789012345678901 2345
     000000000000000000000000000000000000000000 0000
     000000000000000000000000000000000000000000 0000
              CYLINDER SPEED (RPM)
```

Notes: 1. No constraints on yarn properties.
2. Symbol $ is maximum profit per pound,
Symbol 1 is 0.005 $/# less,
Symbol 2 is 0.01 $/# less, etc.

Fig. 32

Maximum Profit/Contract Limit Contours

Input Fiber: Tf = 150/gm, SFf = 13%

5% Contract Limits: Ty < 43.8 /gm, STy > 10.8 gm/tex, CVy < 15.0 %

Maximum Profit = 0.443 $/# under machinery setting at Q = 4 CFM and N = 6900 RPM

```
AIR (CFM)
1.0     5555555555555555555555555555555555555555777777
1.2     5555555555555555555555555555555555555577777776
1.4     5555555555555555555555555555555555557777777766
1.6     5555555555555555555555555555555555577777777766
1.8     5555555555555555555555555555555577777777777666
2.0     5555555555555555555555555555555777777777776666
2.2     5555555555555555555555555555557777777777776666
2.4     5555555555555555555555555555777777777777776666
2.6     5555555555555555555555555557777777777777776666
2.8     5555555555555555555555555777777777777777776666
3.0     5555555555555555555555557777777777777777776666
3.2     5555555555555555555555777777777777777777776666
3.4     5555555555555555555557777777777777777777776666
3.6     5555555555555555555577777777777777777777776666
3.8     5555555555555555557777777777777777777777777666
4.0     555555555555555577$7777777777777777777777777666

5555555555666666666677777777778888888888999999
        012345678901234567890123456789012345678901234 5
        00000000000000000000000000000000000000000000 00
        00000000000000000000000000000000000000000000 00
                        CYLINDER SPEED (RPM)
```

Notes:     Symbol 1 means contract limit for STy is met;
Symbol 2 means contract limit for Ty is met;
Symbol 4 means contract limit for CVy is met;
Symbol 5 = 4+1 means CVy and STy are met;
Symbol 7 = 4+2+1 means all are met; etc.

Fig. 33

Maximum Profit/Contract Limit Contours

5% Contract Limits: Ty < 43.8 /gm, STy > 10.8 gm/tex, CVy < 15.0 %

Maximum Profit = 0.519 $/# is obtained by choosing Tf = 250 /gm and SFf = 7 % fiber processed under machinery setting at Q = 4 CFM and N = 8900 RPM.
Produced yarn properties: Ty = 34.5 /gm, STy = 12.3 gm/tex, and CVy = 12.7%.

Tf (/gm)

```
       50    1 1 1 1 1 1 1 1 1 1 0 0
       70    1 1 1 1 1 1 1 1 1 0 0 0
       90    1 1 1 1 1 1 1 1 1 0 0 0
      110    1 1 1 1 1 1 1 1 0 0 0 0
      130    1 1 1 1 1 1 1 1 0 0 0 0
      150    1 1 1 1 1 1 1 0 0 0 0 0
      170    1 1 1 1 1 1 1 0 0 0 0 0
      190    1 1 1 1 1 1 0 0 0 0 0 0
      210    1 1 1 1 1 1 0 0 0 0 0 0
      230    1 1 1 1 1 0 0 0 0 0 0 0
      250   $ 1 1 1 1 1 0 0 0 0 0 0 0

7 8 9 1 1 1 1 1 1 1 1 1
                 0 1 2 3 4 5 6 7 8 9
                       SFf (%)
```

Notes:  1 = Meet all contract specifications, within 5% or better.
0 = Cannot meet all.

Fig. 34

Maximum Profit for Given Input Fiber Properties, Including Cost.

| Tf /gm | SFf % | Profit $/# | Ty /gm | STy gm/tex | CVy % | Q CFM | N RPM |
|---|---|---|---|---|---|---|---|
| 50 | 7 | 0.451 | 15.5 | 13.1 | 12.9 | 1.6 | 8400 |
| 50 | 13 | 0.454 | 20.5 | 11.5 | 14.6 | 4.0 | 6300 |
| 50 | 19 | 0.408 | 19.6 | 9.9 | 16.0 | 4.0 | 6300 |
| 150 | 7 | 0.479 | 32.3 | 12.9 | 12.7 | 4.0 | 8300 |
| 150 | 13 | 0.443 | 43.8 | 10.8 | 15.0 | 4.0 | 6900 |
| 150 | 19 | 0.366 | 43.5 | 9.2 | 16.6 | 4.0 | 6900 |
| 250 | 7 | 0.519 | 34.5 | 12.3 | 12.7 | 4.0 | 8900 |
| 250 | 13 | 0.447 | 52.9 | 10.2 | 15.2 | 4.0 | 7500 |
| 250 | 19 | 0.346 | 56.2 | 8.7 | 16.9 | 4.0 | 7300 |

METHOD FOR OPTIMALLY CONTROLLING FIBER PROCESSING MACHINES

This is a continuation of application Ser. No. 07/999,212, filed Dec. 31, 1992, now abandoned.

FIELD OF THE INVENTION

This invention relates to the field of control of textile machinery and particularly to a method for the control of textile machinery which enables optimal control of fiber processing machinery to achieve a target operating point.

BACKGROUND OF THE INVENTION

The broad objective of staple yarn manufacturing processes is to convert fibers into yarn. Fibers are, in the most fundamental terms, the materials of construction for yarn. Textile processing machines operate on fibers, in a multiplicity of steps, to prepare them for the final step, conversion into yarn. Within each step there are usually many machines of the same type, as indicated by the numbers in parentheses in FIG. 25. These lists describe typical rotor or ring spinning plants producing 300,000 pounds/week of 25 tex, 100% cotton yarn.

Staple yarn manufacturing processes thus begin with bales of staple fiber and end with yarn. Next comes fabric formation, usually by weaving or knitting means. It is readily apparent that fabric production characteristics and quality parameters depend on yarn quality parameters. Strong and uniform yarns "run better" and are more pleasing to the consumer. Yarn quality parameters depend upon fiber quality parameters and upon machinery performance parameters. Some of these parameters are listed in FIG. 26. Importantly, operating profit for yarn manufacturing depends as much or more on selection of raw materials and machinery operation, jointly optimized, as it does on selling price.

For nearly 50 years, yarn parameter measurement instruments have been available, first for operation in Quality Control (QC) labs and, for about 25 years, for continuously monitoring yarn parameters on certain manufacturing machines. Zellweger Uster, Uster, Switzerland manufactures TENSORAPID and TENSOJET, which measure yarn strength/elongation and Uster Tester 3, which measures yarn evenness or uniformity, hairiness, and fineness (linear density). Some of these QC laboratory instruments have on-line machinery monitoring counterparts. Rieter Machine Works, Ingolstadt, Germany, manufactures OPTRA, a new laboratory instrument which measures trash in yarn.

For fiber parameter measurement, there are increasingly available, over the past 15 years, modern fiber testing instruments which provide multiple data products, are known in the art as High Volume Instruments (HVI), and are manufactured by Zellweger Uster, Knoxville, Tennessee. The primary data products now in use are strength, length, micronaire, color, and trash.

HVI measures fiber properties in the bale state only. Yarn testing equipment measures fiber in the yarn state only. The few on-line instruments in practice measure sliver or yarn uniformity only. The number of measured parameters and machines which are monitored needs to increase dramatically; competitive forces assure that this will happen, especially now that we are in the "Information Age."

Fiber information from HVI and yarn information from TensoRapid have been used to improve performance and profitability of the yarn manufacturing process. These methods are known in the textile industry as, for examples, engineered fiber selection (EFS) or bale information and analysis system (BIAS). EFS software was developed by Cotton Incorporated, Raleigh, N.C., and is sold to textile mills who use primarily United States cotton. BIAS was developed and is sold by Zellweger Uster, Knoxville, Tenn. and Uster, Switzerland. The EFS and BIAS software enable the user to select bales of raw material which can result in better raw materials utilization, fewer processing problems, improved yarn properties, and more profit.

Under carefully controlled conditions, the coefficients of determination ($R^2$) for these multiple linear regression statistical methods relating bale and yarn properties can be as good as $R^2$ ~0.9. This means, under these best of circumstances, that 90% of the variability in the output yarn can be explained by variability in the input fiber properties. More typical results are $R^2$ ~50%, which means that the variations in input fiber properties (the bale state) can only explain 50% of the variations of fiber in the output state, yarn. This means that the 50% which is unexplained is primarily attributable to the variations associated with the processing machinery.

Input-output relationships for EFS and BIAS are based on multiple linear regression statistical techniques which are well known in the art. The output yarn property is typically the single parameter of yarn tenacity or strength. Relationships for other properties are needed.

Since the correlations are established between bale state and yarn state, then, evidently, another limitation of this predictive methodology is that no information is provided on the large number of important intermediate processing steps.

Another problematic feature of this linear regression type statistical approach is that it requires fixed machinery settings and constant production environments. It is a major undesirable consequence that these techniques disguise the influence of the multiple steps of interconnected machinery and their various complicated interactions.

Further, current HVI methods provide average measurements on small bundles of fiber or on the surfaces of fiber masses. Distributions of single entities, fibers or imperfections (neps of several types, trash, bark, grass, etc.), cannot be measured.

Still further, no information is provided on certain important fiber parameters such as trash counts/gram, short fiber content, or neps, etc. These parameters also relate to processing problems, yarn quality, and profit.

The Advanced Fiber Information System, AFIS, was invented in the mid-1980s to provide some of this missing information. AFIS provides distributions of single entity measurements on all fiber states, from bolls on the cotton plant itself to the final fiber state just prior to spinning (steps 7 and 6 in the examples in FIG. 25). Recent and relevant patent and open literature citations are listed in the references. AFIS currently operates in the QC Laboratory, frequently beside yarn test equipment; the next step is on-line monitoring of AFIS measurement parameters. MANTIS is another new instrument which measures single fiber breaking tension, elongation, and diameter and is also described in the references.

AFIS and MANTIS can measure all of the fiber properties of interest in the mill from the bale through the final preparation stage to spinning. This increasingly available new fiber information, in concert with widely available yarn information, has already deepened the understanding of the fiber to yarn engineering process and has improved its quality and profitability in leading mills, worldwide. However, this process has only now begun. There is a growing need for organizing methodology to avoid information overload and according to which better use of the rapidly-increasing fiber and yarn information can be made.

Ultimately, optimal control of the textile manufacturing processes needs to be realized, preferably in real time, from on-line measurements. This makes the need for organizing methodology urgent. Importantly, such methodology is the only practical way to achieve the deepest understandings of the fiber-to-yarn engineering process upon which successful optimal control strategies can be developed.

Conceptualization and development of organizing methodology is not easy. The textile manufacturing process has several unique features which cause the fiber-to-yarn engineering process, and thus optimal control, to be difficult. Among the important features differentiating textile manufacturing processes from others is variability: their input-output relationships are widely diverse and have large random components. That is, the variation from machine to machine or even of the parameters within the raw and processed material are very large. These large random components, relative to deterministic or fixed components, must be recognized as part of the measurement and control problem.

Also, with few exceptions, the operating parameters ("settings") of textile processing machinery have not been made easily variable. It was mentioned above that the machines were assumed to be constant for linear regression predictions. Constant performance has indeed been the objective of machinery manufacturers for nearly a century. One of our points of departure from the current machine design and operation is the recognition that most textile processing machinery can, with redesign, easily be changed dynamically. Some operating parameters can be changed very rapidly, in less than 1 second, for example. This could accommodate the ever present and large random variations of the input fiber material. Being able to adapt to input variations and to produce a more constant output at the same or lower costs (i.e. optimal control) would be a very desirable result not now possible. Availability of optimal control signal information, as described below, provides the necessary incentives to change machinery manufacturers' and mill owners' thinking. This will be appreciated as a major technological innovation.

One can now better appreciate the importance and complexity of the process control problem in yarn manufacturing. That is, given available fiber, with known properties and costs, and, target yarn properties one seeks to determine the settings for which processing performance is "optimal". What constitutes "optimal"? Do we want to manufacture the cleanest yarn? The strongest yarn? The most even yarn? Or do we want to maximize profit? "All of the above" is not a satisfactory answer; most of these objectives are usually in conflict with the others.

Evidently, the purpose of this logical development and the resulting rhetorical questions are to dramatize the fundamentally important and dominating fact that, in all practical cases, over the long term, it is profit that must be maximized. This means that there must be further relationships describing the selling price, or profit, or "benefit" or "value" derived from operating with certain input/output relationships, such as affected by the raw material or by the machinery settings. Stated simplistically and dramatically: it would be most desirable to produce superior yarn while operating the machinery at minimal capital and operating costs and while using less expensive fiber to, thereby, yield increased profit.

Thus the optimization problem is more complex than optimizing physical parameters. Appropriate consideration must also be given to market conditions, to the total capital and operating costs of the plant, even to personnel involved in the manufacturing process. Thus, optimal control means, in the context of this disclosure, maximizing profit subject to constraints imposed by the materials, machinery, and yarn.

Whereas the optimal control problem is large in scope, there are now available powerful technologies to solve it. The rapid development of digital computation means and of advanced statistical analysis means provide good tools. What is needed is a general, practical methodology to organize these tools and modern measurements of fiber and yarn properties into useful methods.

SUMMARY OF THE INVENTION

Accordingly, it is one of our objectives to provide methods whereby rapidly increasing physical and financial information from widely diverse sources could he made more manageable and developed into deeper understanding of and/or used for optimal controls.

It is another objective to more effectively utilize AFIS and MANTIS information and to exploit the modern technology of digital computation and the highly developed methods of modern statistical analysis, including mixed model methodology.

It is a major objective to provide for separate and general statistical models of machinery characteristics and of gross profit characteristics, and to control machines using the models We call those the "$\alpha$-Model", for the machinery, and the "B-Model", for gross profit. Our ultimate objective was to provide for step-by-step determination of the elements of the models utilizing modern fiber and yarn testing instruments and financial information, while recognizing and handling ever-present, large random or noise components.

It became a further objective, given our models for the fiber processing machinery and the profit generated by operating it, to use modern statistical methods to search for the best, or most profitable, or optimal operating conditions. That is, one searches for processing conditions which produce the highest profit subject to other constraints, such as minimum yarn strength, maximum yarn trash, or other contractual terms between yarn manufacturer (seller) and yarn user (buyer). Similarly, one controls operation of machinery to produce the highest strength yarn, or the most even yarn or the cleanest yarn. These are only a few examples of objectives for optimal control strategies.

The methods disclosed herein enable modelling the entire yarn manufacturing process, from bale selection to "bottom-line" profit. We shall specifically disclose the methodology for determining and applying for the $\alpha$-Model for the open end or rotor spin box. This is exemplary of modelling other textile processing machines. All of them can be modelled according to our methods and all of the individual models can be combined into a powerful composite model for the entire process. Most importantly, the $\beta$-Model is determined and applied according to identical procedural steps.

The above and further objectives are realized in a method corresponding to a preferred embodiment of the present invention. In a preferred embodiment a method for the optimal control of textile manufacturing processes is accomplished by measuring the process physical performance parameters, with modern fiber and yarn test equipment and monitoring instruments, and process financial performance, with modern manufacturing, and marketing software. There are three categories of interest in the operation of the process machines over which the operator exercises some degree of control. The first category is the input material to each process machine or step, beginning with baled fibers, the second group of variables is the machine settings and the third group of variables is the quality characteristics of the output fiber or yarns, including costs and prices.

The first step in a preferred embodiment is a CALIBRATION Step and involves operating the manufacturing process over the full range of input fiber, machine settings, and output fiber or yarn characteristics, including costs and prices, and developing a data base of the entire process performance over this range.

In the second major step of the preferred embodiment, OPERATION, a target operating point (TOP) is selected. Predictive models for process parameters and for profit parameters are established, based on the calibration data from the first step, and on the variables defined relative to the target operating point. During operations in the preferred embodiment, one continuously makes various physical and financial measurements at various times (and of various qualities), inputs these data into the predictive models and determines the departure from the target operating point. Either manually or automatically, the machinery or input fiber parameters are adjusted to achieve optimal conditions relative to the chosen target operating point. If any of the major parameters change, such as input fiber characteristics or contractual terms for sales of the yarn to be sold, and as new measurement data become available, a new, refined target operating point is established and the process continues with these improved predictive abilities.

In a further embodiment of the present invention the method is totally automated wherein the various measurement physical and fiscal are made while the precess is on line and the calculations are rapidly done in a modern computer environment. The computer generates the appropriate control settings and transmits them to the automated machinery to implement our method onto the "fly".

BRIEF DESCRIPTION OF THE DRAWINGS AND TABLES

The above and further features of the invention may best be understood with reference to the following Detailed Description of a preferred embodiment of the invention and the drawings and tables in which:

FIGS. 2A and 2B are diagrammatical view of an improved opening section for a "spinbox" of an open end or rotor spinning machine;

FIG. 3 is a graph which illustrates a machinery characteristic relating trash in the fiber input to trash in the fiber state or yarn output;

FIG. 4 is a graph illustrating the parametric sensitivity of a generic spin-box;

FIG. 5 illustrates the parametric sensitivity of yarn trash content;

FIGS. 6A–14D are graphs representing machinery and gross profit characteristics with fixed parameters and varying parameters;

FIGS. 15–18 are graphs of machinery characteristics for various parameters for a second stage in the spinbox process;

FIG. 25 presents the various processing steps which fibers undergo in the process of spinning yarn with ring spinning machinery and with rotor spinning machinery;

FIG. 26 provides a list of the main quality parameters of the various components of the process of spinning yarn or making fabric;

FIG. 27 presents the process and profit characteristics M and P of machinery in equation form;

FIG. 28 is a listing of the various input and machinery characteristics, and initial target operating points, and $\alpha$-Model elements derived from Equation set 2;

FIG. 29 compares $\alpha$-Model predictions, with large noise components, to exact, noise-free results based on Equation set 2;

FIG. 30 is a table giving coefficients of determination ($R^2$) between machinery characteristics M and the $\alpha$-Model;

FIG. 31 provides a contour plot for optimum conditions and operating settings;

FIG. 32 shows maximum profit/contract limit contours wherein the operating conditions are limited not only by attempting to achieve maximum profit but falling within certain contract limits of the output yarn;

FIG. 33 is a maximum profit/contract limit contour table similar to that of Table 8 arranged with respect to trash content and short fiber content; and FIG. 34 is a table showing maximum profit for given input fiber properties including cost.

DESCRIPTION OF A PREFERRED EMBODIMENT

A. Modelling the Rotor Spin Box

By modelling we mean that the input and output fiber or yarn parameters can be measured with such QC Laboratory instruments as AFIS, MANTIS, HVI (for bale state), TENSORAPID, Uster Tester 3, and OPTRA, or with their on-line counterparts, that the machine operating parameters such as opening cylinder speed and air flow can be measured and controlled, also according to known methods, and that external market conditions and internal cost accounting information can be measured. Given this information, from diverse sources and of widely-ranging types, our optimal organizing methodology proceeds generally along lines of statistical process control and statistical control system theory. One advancement over prior art methods is a general method for the determination of elements of separate models characterizing the process machines and profits from the business, when both are operating around so-called "Target Operating Points", or TOPS.

We now bring the focus of our disclosure to physical models for the machinery characteristics. The most important objective of the remainder of this disclosure is to show, step-by-step, our methods according to which the elements of the $\alpha$-Model are established with available fiber and yarn test equipment. The determination of the $\beta$-Model elements follow identical procedures. In conclusion, we shall demonstrate the usefulness of both.

Figure 1:
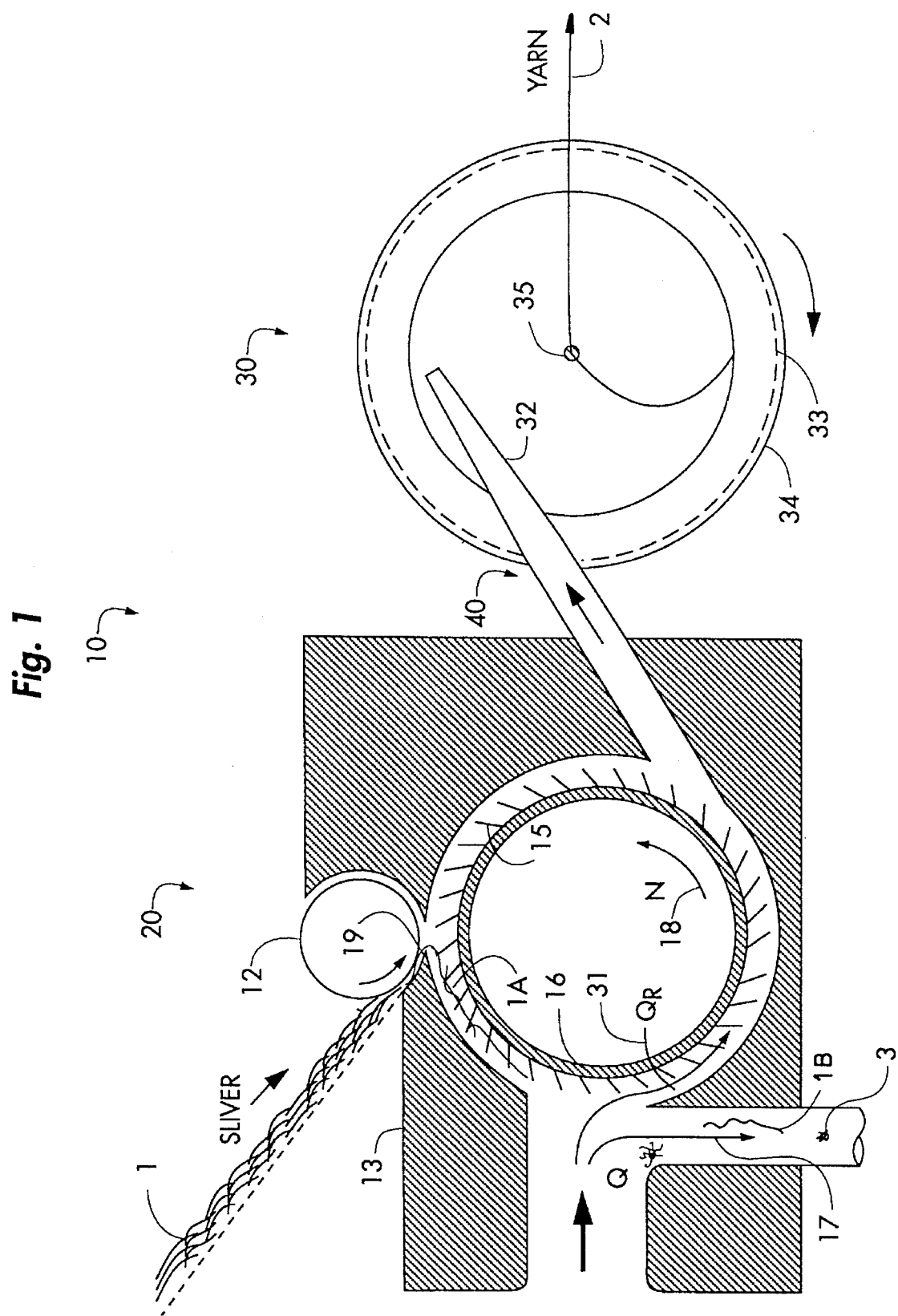
FIG. 1 is a diagrammatical view of the "spinbox" of an open end or rotor spinning machine.
Figures 6A, 6B, 6C, 6D:
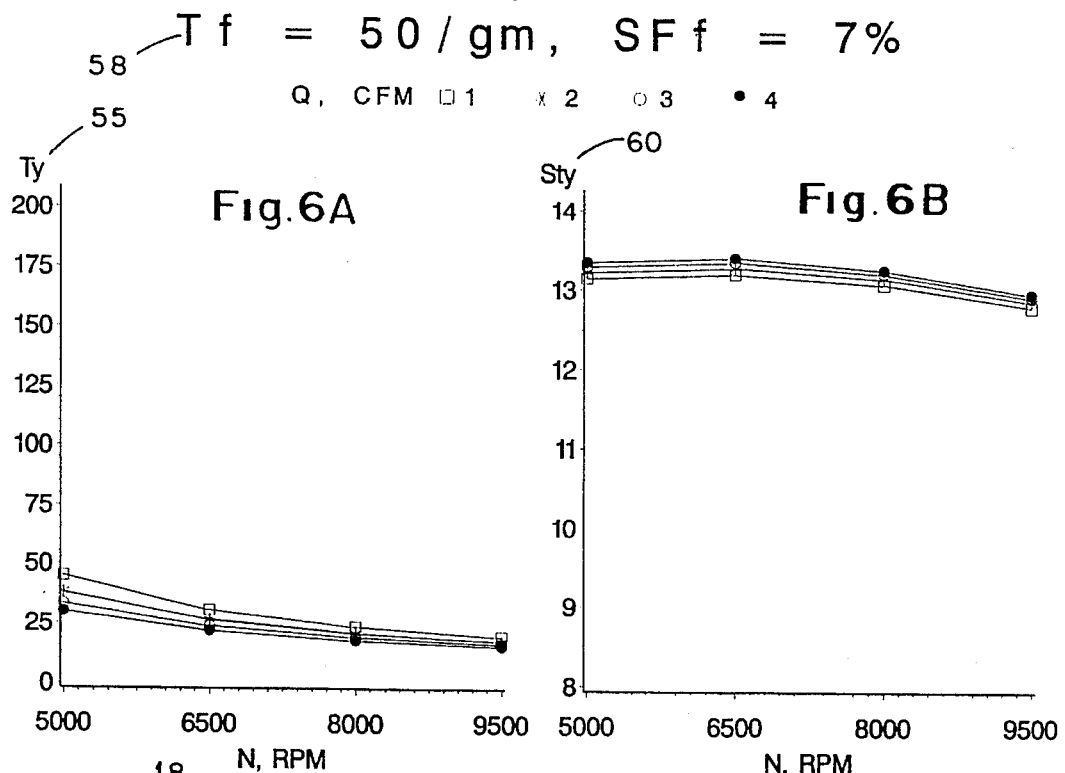
Figure 7A:
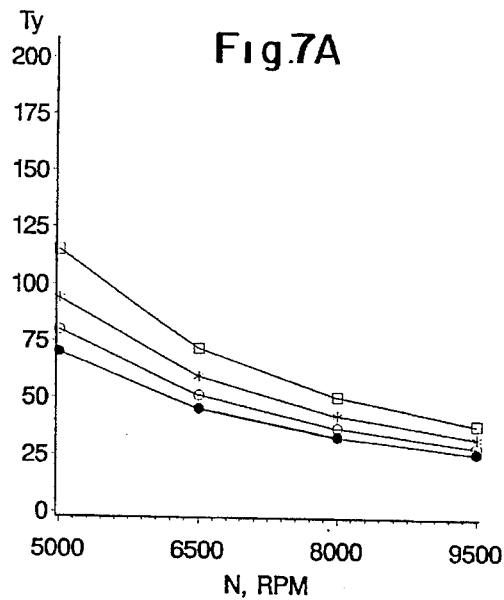
Figure 7B:
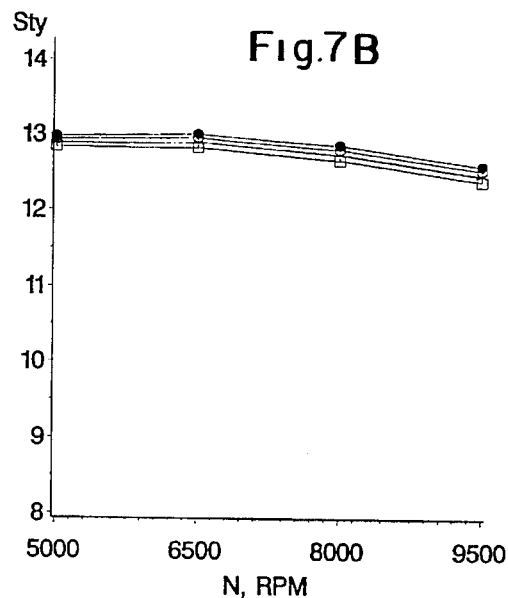
Figure 7C:
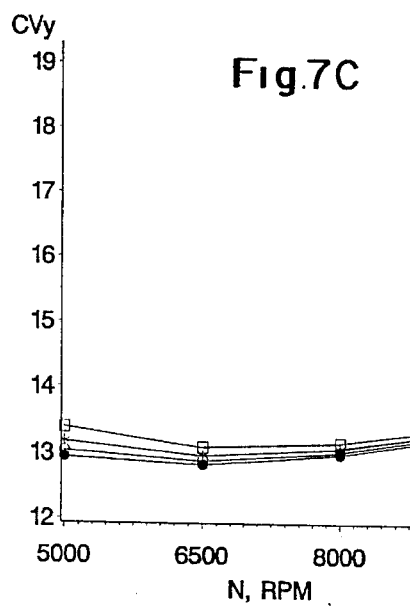
Figure 7D:
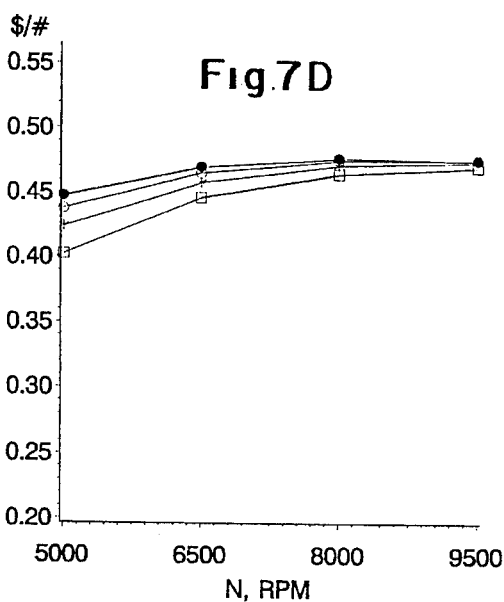
Figure 8A:
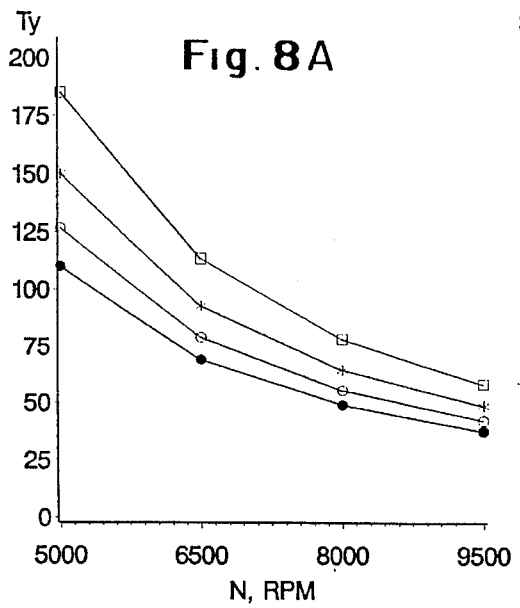
Figure 8B:
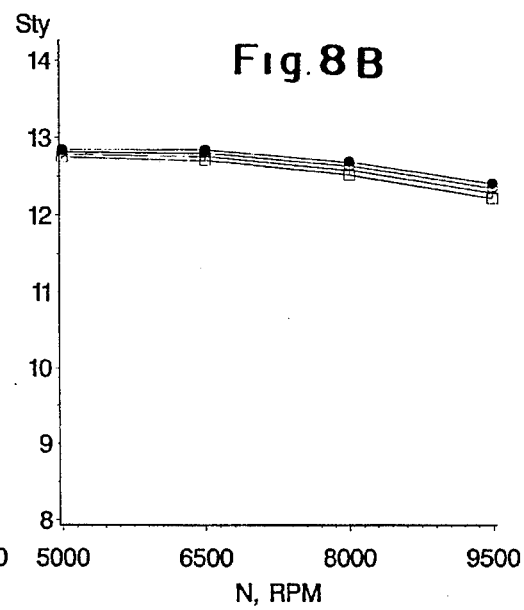
Figure 8C:
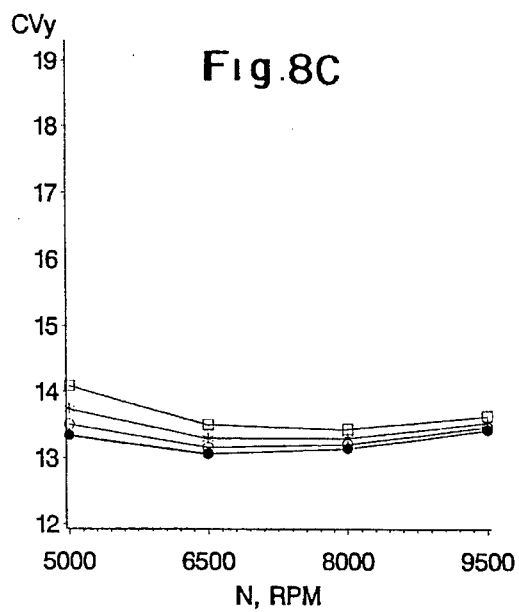
Figure 8D:
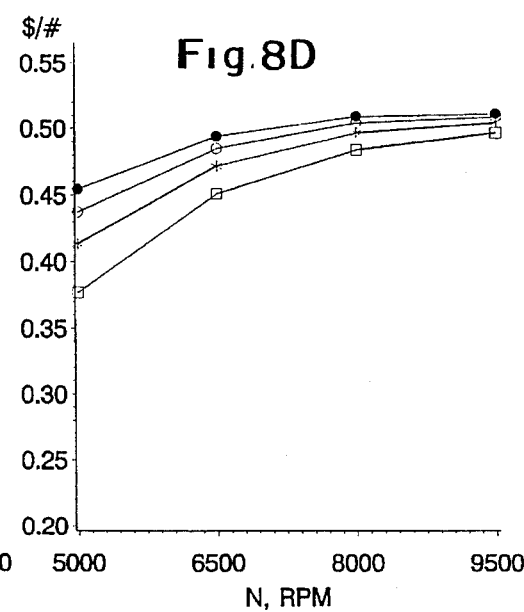
Figure 9A:
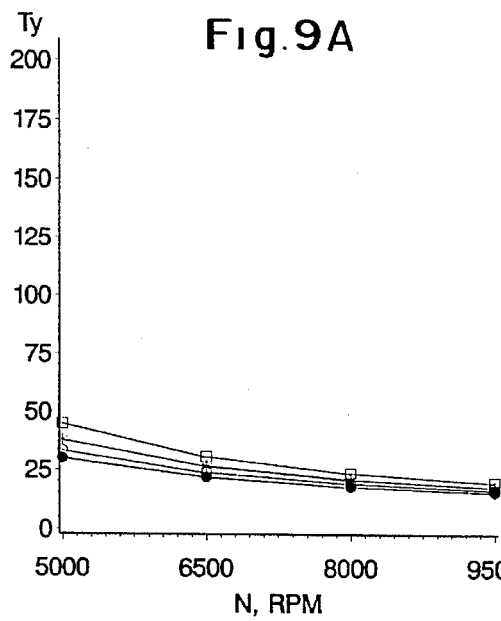
Figure 9B:
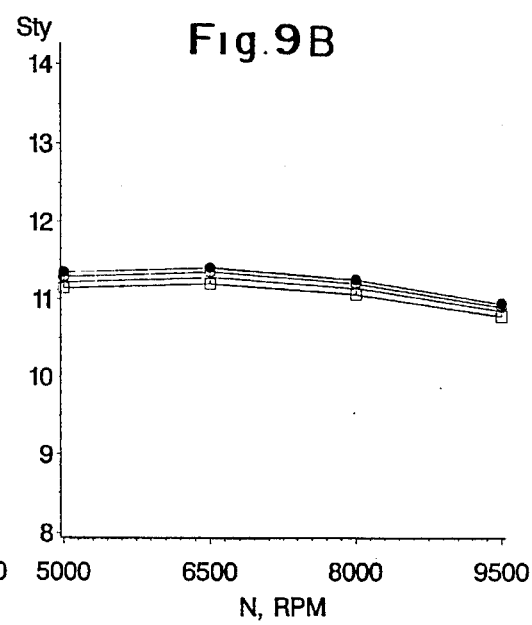
Figure 9C:
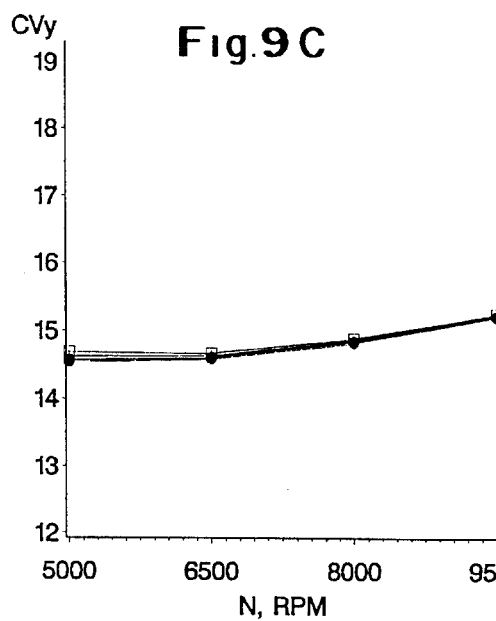
Figure 9D:
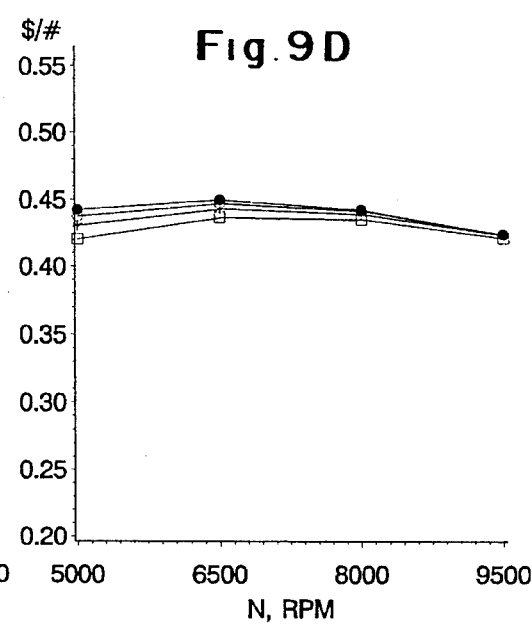
Figure 11A:
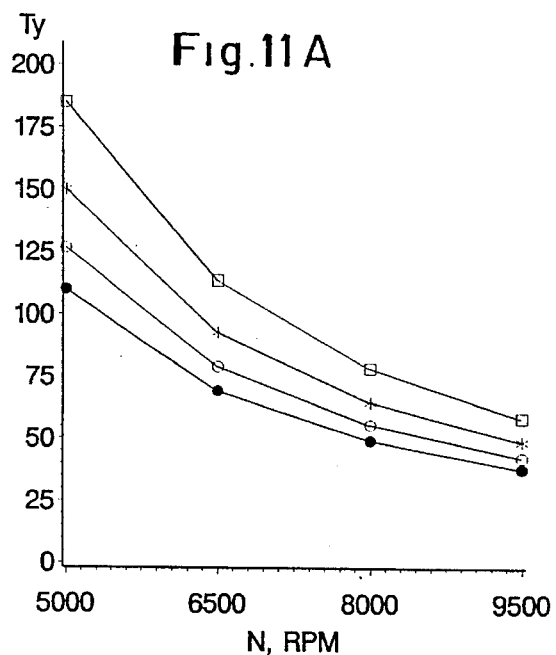
Figure 11B:
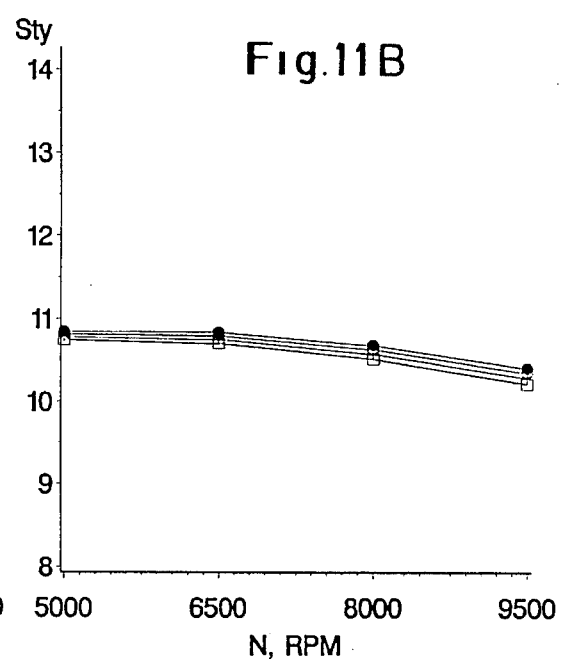
Figure 11C:
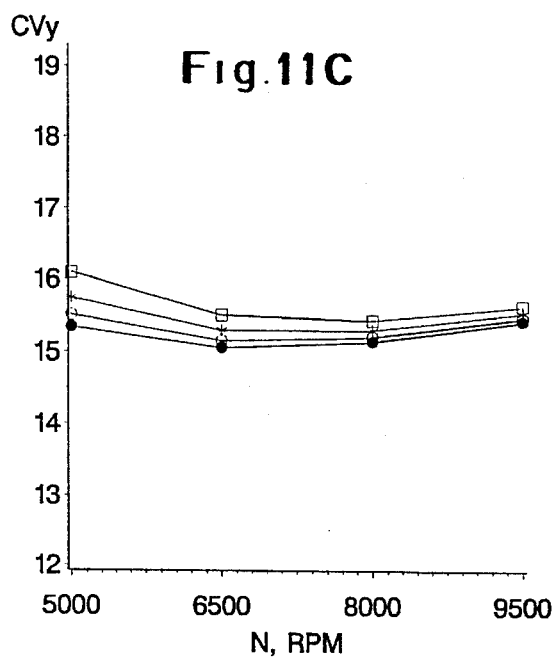
Figure 11D:
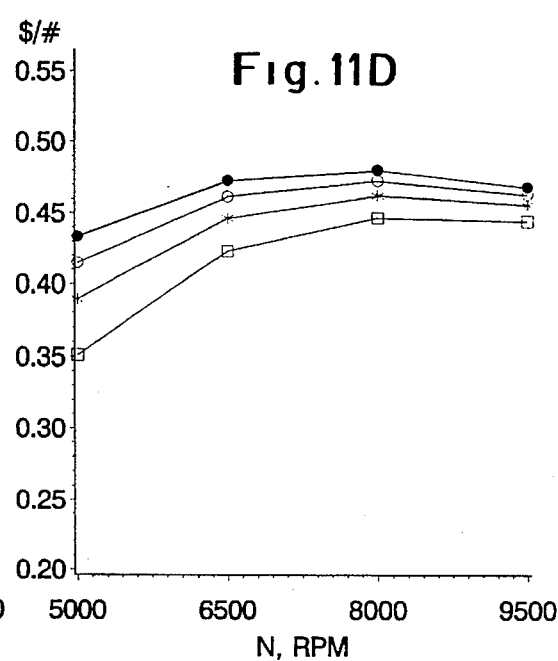
Figure 12A:
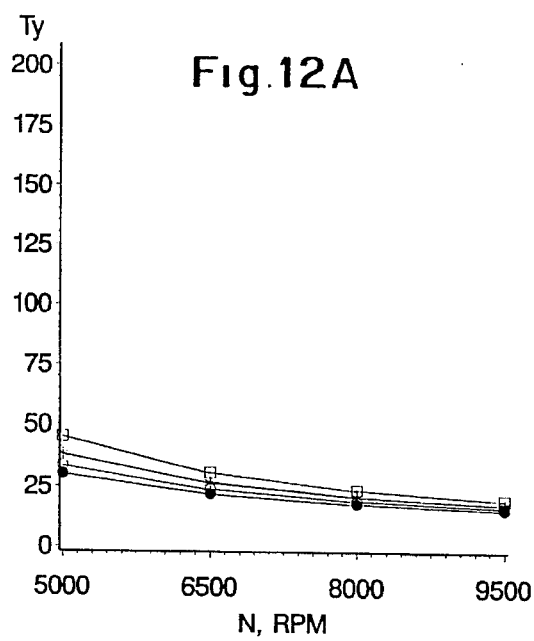
Figure 12B:
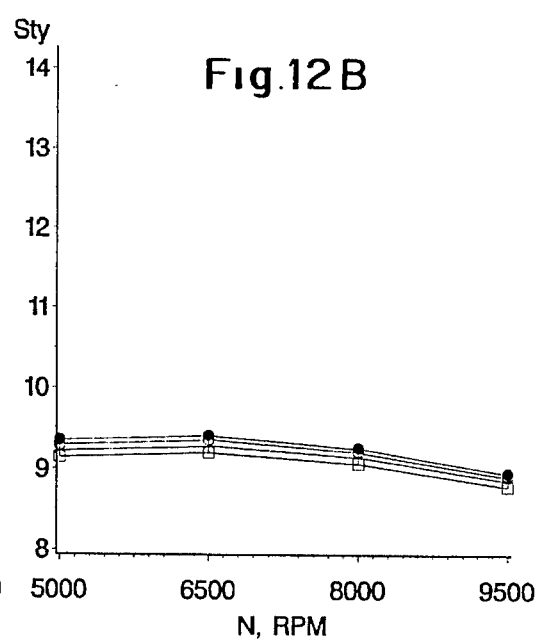
Figure 12C:
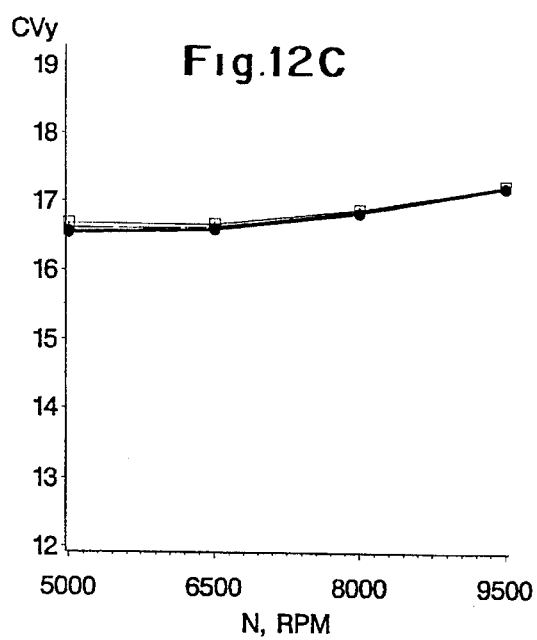
Figure 12D:
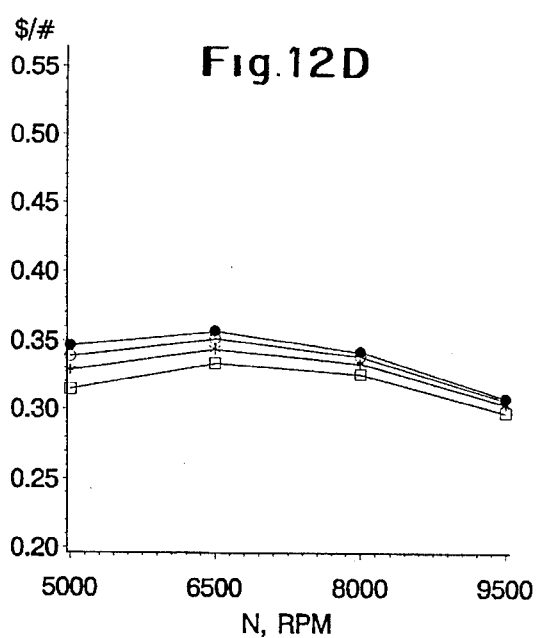
Figure 13A:
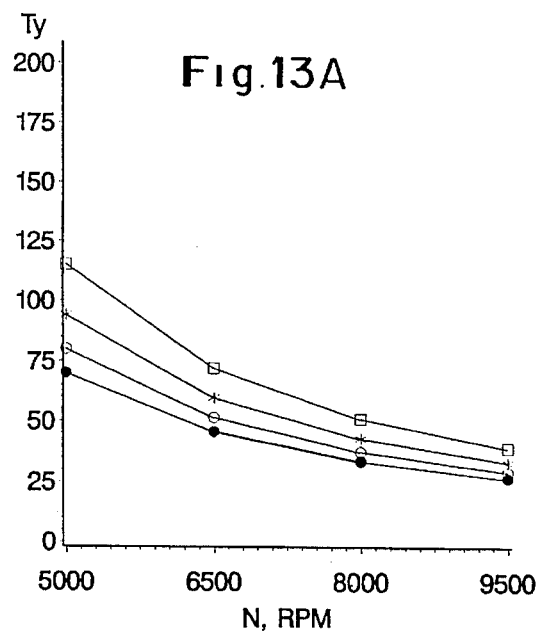
Figure 13B:
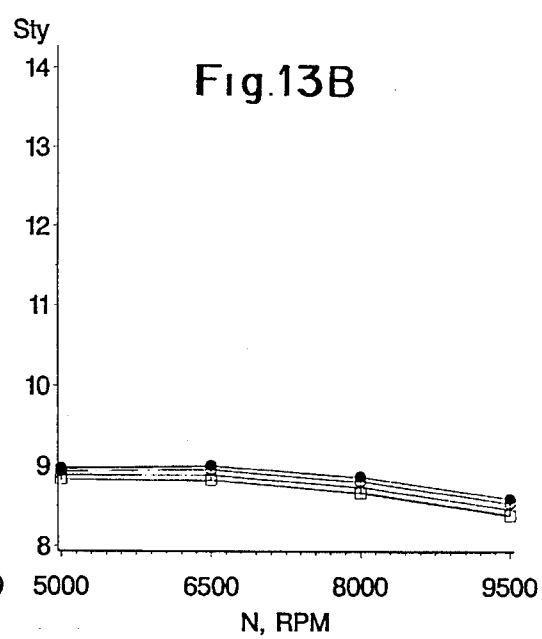
Figure 13C:
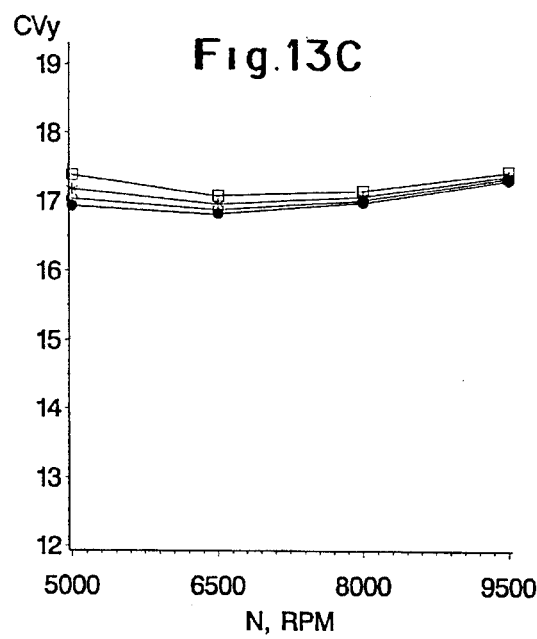
Figure 13D:
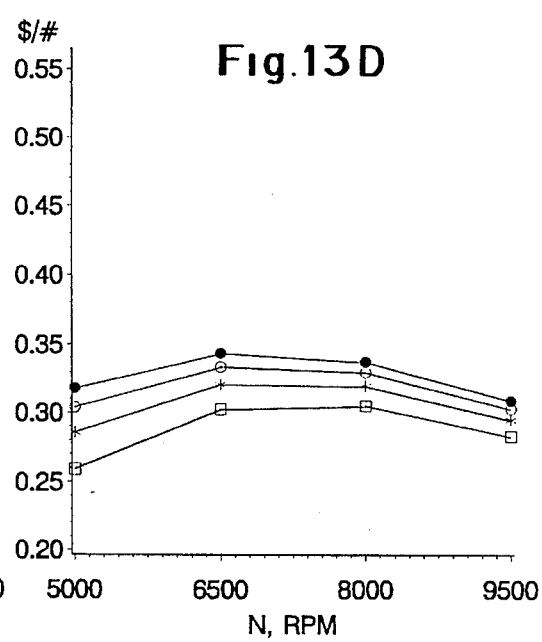
Figure 14A:
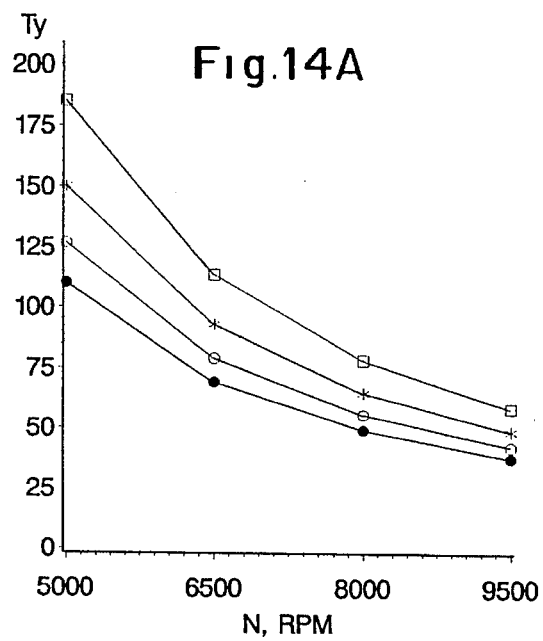
Figure 14B:
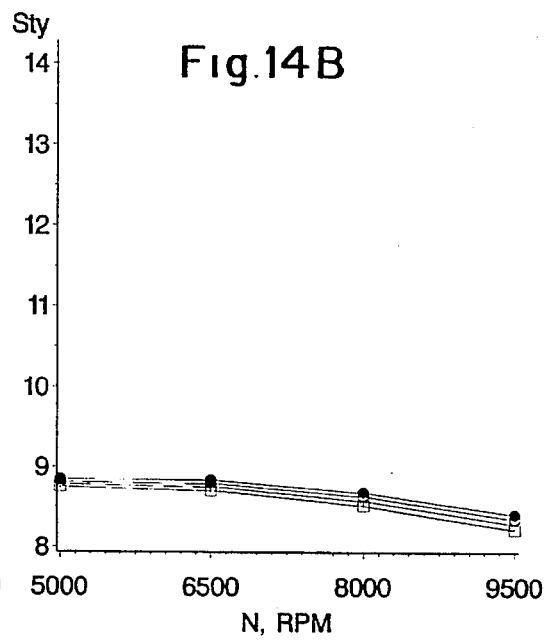
Figure 14C:
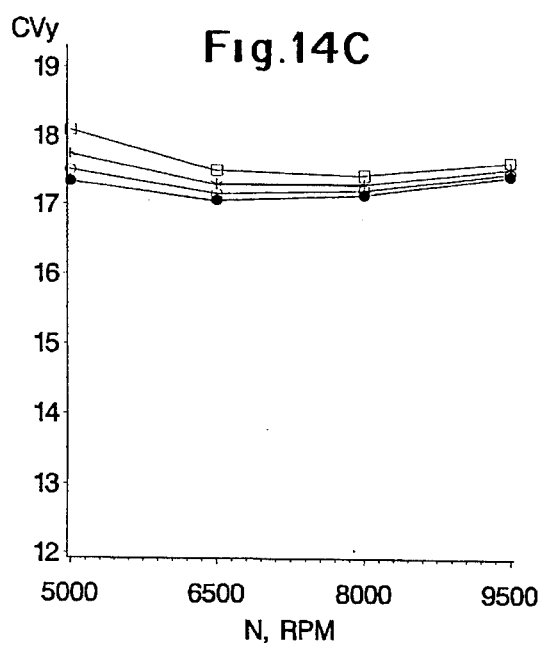
Figure 14D:
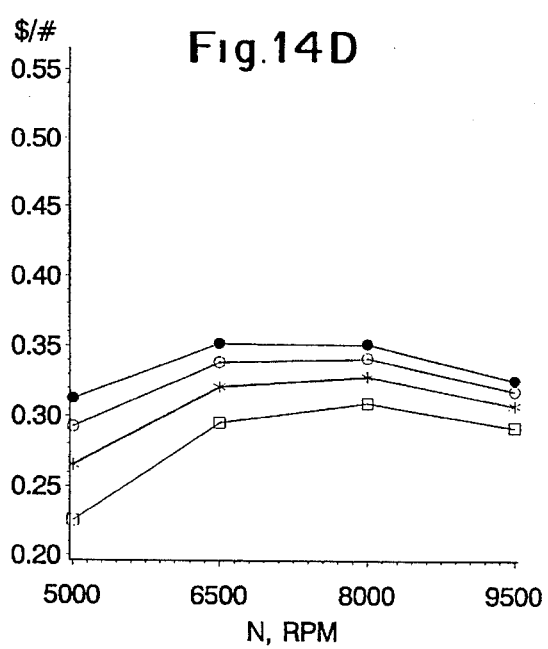

FIG. 1 diagrams generically the "spin-box" of an open-end or rotor spinning machine. This "spin box" 10 consists of two steps, an opening/cleaning stage 20 followed by a rotor spinning stage 30. The elements of FIG. 1 are generically representative of current-design rotor spinning machines except that the rotational speed N 18 and trash transport air flow rate Q 17 are variables here. An overview of the process which converts fiber in the sliver state 2 into fiber in the yarn state is now given.

Importantly, emphasis is placed upon the machine characteristics of opening section. This processing step is almost functionally identical to the AFIS fiber individualizer. We assume that the fiber leaving the opening section is correctly spun into 25 tex yarn (less any small losses.) The output yarn properties are, of course, affected by the fiber properties entering the rotor and by its various speeds, air flow, groove design, etc. Modelling the rotor spinning process would follow similar procedures in accordance with our method, as do all other fiber processing machines.

Sliver 1, consisting of generally parallel fibers with a linear density of about 5 grams per meter, is introduced to the feed roll 12 and feed plate 13 region. The fibers 1A are engaged by the pins or combing wire 15 on the opening cylinder 16 and trash particles 3 in the fiber 1A are ejected by impact and centrifugal forces. The air flow Q 17 transports the ejected trash 3 out of the system. Accompanying the ejected trash particles are, unfortunately, small amounts of good fibers 1B. This opening/cleaning stage 20, like all such stages in textile processing, suffers from the difficult trade-off between opening and cleaning performance versus fiber loss and damage. Cleaning efficiency can be improved by increasing the speed of the opening cylinder N 18. But this will also cause more good fibers to be thrown out. Increasing Q 17 will cause more trash to be extracted. But increasingly Q 17 also extracts more good fibers. Indeed increasing either the trash extraction flow Q 17 or the opening cylinder speed N 18 will increase the amount of trash removed but these increases will also increase the amount of good fiber removed.

Increasing the speed N 18 of the opening cylinder 16, to remove more trash or to improve combing effects, both positive impacts, has unavoidable negative impact. Fibers 1A are held around the nose 19 of the feed plate 13 and are engaged by the combing roll 16 for relatively long periods of time. They are held until they are released by the feed roll/feed plate 12/13 combination; such times are about 1 second. It follows that fiber damage, all other things being equal, will increase as the speed N increases. Increasing fiber damage is reflected in increased short fiber content, the percent of fibers whose length is less than 0.5 inch. Both yarn strength and evenness suffer as short fiber content increases. This is yet another complex trade-off that must be dealt with in machine design and operation.

It is sufficient for a proper understanding of the method to explain only two variable machine settings or parameters, Q 17 and N 18. Numerous other parameters, including the type and density of the wire or pins 15 on the cylinder, or tolerances and spacings, and the like, have positive and negative impacts that must be carefully considered in machine design and operation trade-offs. We limit the considerations to N 18 and Q 17 to make this presentation simpler and clearer but note that any number of machine variables can be handled by our method. For example, we show in FIG. 2A an improved opening section 20A for the spinbox 10. The improvements are based on our experience with the AFIS fiber individualizer. The major innovations of this design are that additional controllable parameters have been introduced which will improve the performance of the apparatus. One is a moving carding flat 21. Others are the introduction of a perforated opening cylinder 16A and counterflow slots 22, as now used in AFIS.

After opening and cleaning by the opening/cleaning stages 20 or 20A, the more or less individualized fibers and remaining trash and other imperfections are transported by a flow $Q_R$ 31 to the rotor section. This flow $Q_R$ 31 is generally in the range of 5 CFM and is driven by suction means (not shown) in the vicinity of the rotor. For this disclosure $Q_R$ 31 is constant at 5 CFM. The fibers leave the transport tube 32 and are thrown into the groove 33 of the rotor 34 as illustrated in the cross-section in FIG. 2B. The yarn 2 is formed in the groove of the rotor and withdrawn from the navel 35 of the rotor 34. Twist is imparted by the rotor's rotation.

In our physical considerations of the spinbox performance we shall assume that the trash and short fiber content in the fiber, in the intermediate stage 40 following opening/cleaning 20, remains substantially unchanged as the fiber moves into the spinning stage. Treating the spinbox 10 in these two stages illustrates the concept of sequential machinery steps or stages. For our purposes the action of the rotor 34 is to convert the intermediate fiber state, designated 2, into yarn. As stated above, measurement instruments are now available which permit the measurement of fiber properties at every point in the staple cotton manufacturing process from the boll though the final stage of preparation. AFIS enables the measurement of trash and short fiber content, the only two input variables used in this discussion. Of course, many other fiber parameters can be measured with AFIS, MANTIS, or other instruments; these measures can be included in our methods.

FIG. 3 illustrates a machinery characteristic 50 relating trash in the fiber input to the spinbox $T_f$ 51 to trash in the fiber state or yarn output from the spinbox $T_y$ 52. Fiber trash content is measured with AFIS and yarn trash content is measured with OPTRA. These data are from co-inventor Anja Schleth's thesis "Untersuchung der Zusammenhänge Zwishen Faser und Garnprüfungen mit Schwerpunkt Nissen—and Trashprüfung," Fachhochschule Reutlingen, Germany. (Examination of the Relationship Between Fiber and Yarn Measurements, with Emphasis on Nep and Trash Measurements.") and represent the relationship between trash in the yarn and trash in the fiber for three different rotor spinbox types, symbols 3, 4, 5 in FIG. 3. All of the speeds and air flows were fixed, as is normal. (Two sets of data for ring spinning are also shown as symbols 1 and 2. These readings are not included in the calculation for coefficient of determination, $R^2$.

FIG. 4 illustrates the parametric sensitivity of our generic spinbox to varying the speed from 5,000 to 9,500 RPM. "Machinery characteristic" equations which produce these curves are described later. Evidently, as speed N 18 is increased, the yarn trash content $T_y$ 53 is reduced due to the improved cleaning efficiency of the opening cleaning stage 20. FIG. 5 illustrates the parametric sensitivity of yarn trash content $T_y$ 54 when the air flow 17 is varied from 1 to 4 CFM. Again, the yarn trash content is reduced with increasing air flow.

FIGS. 6A through 14D show yarn trash count $T_y$ 55 versus opening cylinder speed N 18. These graphical representations 56 give descriptions of machinery characteristics that are more useful for the present disclosure, particularly from the point of view of optimal machine control. That is, for a given fiber trash input $T_f$ 58, one may determine from the speed and air flow settings what the output yarn trash content will be. A similar family of curves may be drawn using Q as the independent variable and N as the family-generating parameter, but the form of Ty versus N in FIGS. 6 through 14 is better for this disclosure. Similar comments apply to the other graphics in FIGS. 6A–14D giving Yarn Strength $ST_y$ 60, yarn Coefficient of Variation $CV_y$ 62, and gross profit per pound $/# 64.

Such two-dimensional curves define the machinery characteristics for the variables N and Q. Of course, many other variables which affect yarn trash could be similarly anticipated and plotted. We shall use parametric curves of the form of FIGS. 6A–14D below to describe the machinery characteristics of the generic spinbox in order to disclose our methods for determining elements of general models for fiber processing machinery.

If one were only concerned with yarn trash content, the conclusion, from examination of the machinery characteristics in FIGS. 6A through 14D, is to operate at the highest speed and air flow settings since these correspond to the lowest trash content in the yarn. In this example optimal control would simply reduce to operating at the extremes of the machine's ranges of settings. This conclusion is recognized as nonsense; increasing speed and air flow have their negative impacts as well as the positive impact of improving the cleaning efficiency; trade-offs between these positive and negative effects must be made.

For yarns spun from staple fibers, the purposes of the several stages or steps of fiber processing machinery (See FIG. 25) are to prepare the fibers for the final step, spinning. Each machine, except the first, takes in fiber from the output of previous steps. (Of course, the bale state is itself the output of gin processing machinery.) Alternatively, each machine's output is the input to the next set of machines. Each machine thus has fiber inputs and fiber outputs whose properties may be measured, along with its operational settings or parameters. Yarn is the fiber state resulting from the spinning machines.

Processing machine characteristics have a functional relationship between input properties, machine settings, and output properties of the form $$F_{i+1} = M_i(X_i, F_i) \tag{1}$$

where $F_{i+1}$ is a vector of values of output or fiber (yarn after the last step) properties, $X_i$ is a vector of values of the i-th machine settings, $F_i$ is a vector of values of input fiber properties, and $M_i$ describes the functional relationship which we shall call machinery characteristics. The fiber or yarn properties at either the machine input or output, and the machine settings, can be measured on-line (while the machine is running). Off-line (in the laboratory), fiber and yarn properties can also be measured; this is more commonplace now. These measurements include random errors or noise. The relationship M can be used to optimally control fiber processing operations if it is known sufficiently accurately and precisely.

The machine characteristics M can be determined experimentally. Such experiments involve the acquisition of measurements $F_{i+1}$, $F_i$, and $X_i$, where i is an integral index increasing from 1 and denotes the various machine steps or the input thereto. In FIG. 25, for rotor spinning, i=1 corresponds to bale state and i=7 corresponds to finish drawing sliver. For rotor spinning $F_8=Y_2$ (yarn). The structure of the functional relationship or machinery characteristics M may also be either partially hypothesized from the various laws of physics or known from expert knowledge of machine behavior. In the rotor spinbox model presented below, M is a system of equations based on measurement and experience, especially with AFIS.

We shall model the machinery characteristics relative to operating points. We call this model the "α-model" and our discovery yields model elements which are determined from measurement data of input fiber, output fiber, and machinery settings.

To illustrate our method, we first provide the functional relationship M for the generic spinbox machine of FIG. 1 commonly used by the industry to convert processed fiber (sliver) into yarn. The functional relationships M are based upon the current state of knowledge of the opening section 20, which is functionally similar to AFIS, of general spinbox 10 physics and expert knowledge of the process, and of rotor spun yarn properties, as described in the Zellweger Uster publication "Uster® Statistics 1989." The functional relationships M, hereafter referred to as the machinery characteristics M, are the smoothed, noiseless curves in FIGS. 4 through 18, which are plots from the machinery characteristic M provided in FIG. 27 as Equation Set 2. We shall later use the machinery characteristic equations, by appropriately adding large components of noise to all measured parameters, to generate synthetic measurement data similar to what can be expected with real world measurements.

FIG. 27 also contains profit model P, to be explained below.

The P ($/#) shown in Equation Set 2a in Table 3 and plotted in FIGS. 4 through 14D is to be interpreted as gross profit, in dollars per pound of yarn. Gross profit is the yarn selling price minus costs of goods manufactured, on a unit weight basis. The raw material cost adjustment C shows the benefits of buying less expensive raw materials, those having high trash and short fiber content in the bale. The raw materials parameters used here, for clarity, are the trash and short fiber content at the spinbox input, not in the bale, and the cost advantages ranging from 0 to $0.20/# are also at the spinbox input and therefore reflect the net advantage of paying less for high trash raw stock but losing more in cleaning. For simplicity, we assume that the material cost at the spinbox input is $1.00/#. Thus the monetary loss associated with losing good fiber is simply 0.01L.

In this example, the spinbox 10 in FIG. 1 processes sliver 1 which is characterized by two measurable properties: input fiber trash content, represented by the variable $T_f$, and input fiber short fiber content, represented by the variable $SF_f$. Both properties are measurable with AFIS. Thus, high values in the bale translate to high values at the spinbox input. The spinbox 10 produces fiber to an intermediate stage 40, denoted stage 2, at which point additional measurements can be made. Fiber at stage 2 can be characterized by two measurable properties; stage 2 trash content, represented by the variable T2, and stage 2 short fiber content, represented SF2, as seen in Equation 2a, FIG. 27, and in FIGS. 15–17. Both properties are measurable with AFIS.

The spinbox 10 is assumed to have two machine settings. These are opening cylinder speed N18, and trash transport air flow rate, Q17. These machine settings can be made with a good accuracy and precision. We interpret the values of N and Q as the actual cylinder speed and air flow without random measurement error or noise. More rigorously stated: the large random effects in fiber and yarn measurements dominate, so little is lost by assuming perfect measurements of N18 and Q17.

Yarn 2 properties are measured with TensoRapid or TensoJet (strength/elongation), Uster Tester 3 (evenness, hairiness, fineness, imperfections), or OPTRA (trash particles per kilometer or trash particles per gram). We are here concerned with the three yarn properties $T_y$, $St_y$, and $CV_y$.

An additional property of the generic spinbox machine is that a small fraction of fiber is lost during processing. This fiber loss fraction, represented by the Function L in Equation Set 2 in FIG. 27 and shown in FIG. 18, depends upon the machine settings N and Q. Lost fiber fraction is measured by weighing the input fiber before processing and the output yarn after processing and calculating $$L = \frac{W_f - W_y}{W_f} \tag{3}$$

where $W_f$ is the weight of input fiber and $W_y$ is the weight of the yarn produced from the input fiber, when both are collected for equal times, and L is the measured fiber loss fraction.

B. Composite and Matrix Representations for Machines Connected in Series

Figure 19:
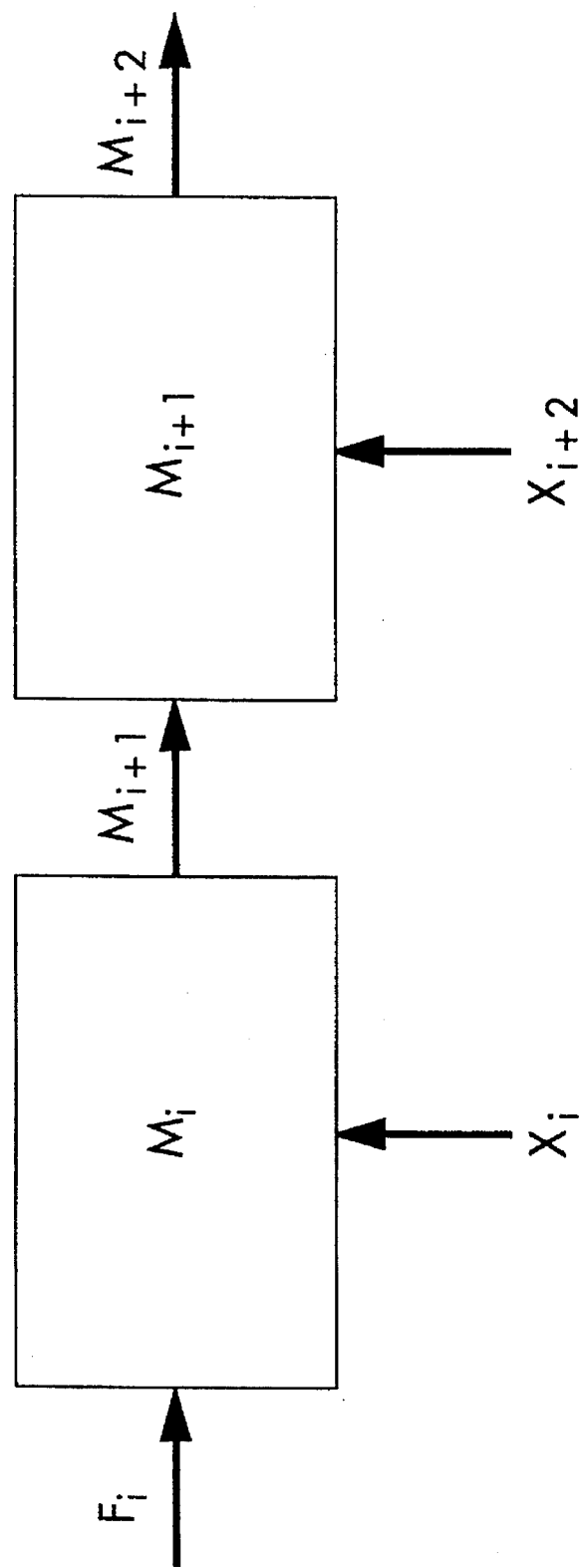
FIG. 19 is a schematic block diagram showing the functional relationship between machines operating in series.

If two machines operate such that the second machine further processes the output of the first machine to produce the second machine's output, then the machines are connected in series. Schematically, this is shown in FIG. 19. If each machine is defined by its characteristic equation, Equation 1, then $$F_{i+1} = M_i(X_i, F_i)$$

$$F_{i+2} = M_{i+1}(X_{i+1}, F_{i+1}) \tag{4}$$

and given that the output of machine i is the input of machine i+1, then a composite model can be defined by $$F_{i+2} = M_{i+1}[X_{i+1}, M_i(X_i, F_i)] \tag{5}$$

This is functional composition and can be expressed in the shorthand notation $$F_{i+2} = M_{i+1} o M_i(X_{i+1}, X_i, F_i) \tag{6}$$

This approach can be generalized to an arbitrary number, p, of machines connected in series $$F_{p+1} = M_p o M_{p-1} o \cdots M_1 (X_p, X_{p-1}, \cdots X_1, F_1) \tag{7}$$

Defining a composite vector of machine settings $X_a$, given by $$X_a = \begin{bmatrix} X_1 \\ --- \\ X_2 \\ --- \\ \cdot \\ \cdot \\ --- \\ X_i \\ --- \\ \cdot \\ \cdot \\ X_p \end{bmatrix} \tag{8}$$

where each $X_i$ is assumed to be a column vector, and the horizontal dashes between the $X_i$ indicates that the partitioned vector $X_a$ is formed by stacking $X_1$ on top of $X_2$, etc., then the aggregate machine model $M_a$ is given by $$F_{p+1} = M_a(i \ X_a, F_1) \tag{9}$$

where, in shorthand notation, $$M_a = M_p o M_{p-1} o \cdots M_2 o M_1, \tag{10}$$

(Note: Matrix operations are a special case when equations are linear.)

In maximizing benefits with our method, one or more machines, or portions of machines, may be represented in the aggregate by a functional representation M. This representation will still describe the behavior of machine outputs, which may now include the outputs of intermediate stages of processing, such as the stage 2 fiber properties of the example spinbox machine, in response to machine settings and the properties of machine inputs. Based upon this composition model a value function can be used to describe the benefit, or profit efficiency, etc. of operating the machine at particular machine settings and consuming particular raw materials or inputs.

The equations relating input fiber properties and machine settings to stage 2 fiber properties, and the equations relating stage 2 fiber properties to output (i.e., yarn in this case) properties, can be combined by substitution of variables, according to the procedures of functional composition. The resulting equations describing the generic spinbox machinery characteristics M are those given in Equation set 2, FIG. 27.

C. Modelling with Respect to Target Operating Points ("TOPS")

The Equations in FIG. 27 specifically define one exemplary rotor "spin-box" machine characteristic M as previously described generally in Equation 1, $$Y = M(X, F), \tag{11}$$

where $F_{i+1} = Y$, the yarn state in this case. We will drop the i subscripts now since we are concerned with only one machine type.

One wishes to control machine settings and input fiber selections to maximize profit (i.e., to control means to choose, or to manipulate, or to set, or to take actions). These actions have positive and negative consequences. As defined earlier, optimal control means taking these actions which maximize profit subject to fiber and machine constraints.)

Given an appropriate and similarly-determined model P for calculation of profit, then maximizing P, subject to constraints on F and M, would be a standard optimization problem. However, neither the process machine characteristics M nor the profit characteristics P are known well enough to enable application to specific machine steps or to specific, total mills. Both M and P must be determined specifically and frequently. M is observed by measurement, at various times, of input fiber properties, F, output fiber or yarn properties, Y, and machine settings X. In addition, profit characteristics P are available at various times as are costs of production and the selling price of the output, yarn. From these various measurements must come all information used to maximize profit. It can thus be appreciated that "information overload" results from standard optimization methods.

Figure 20:
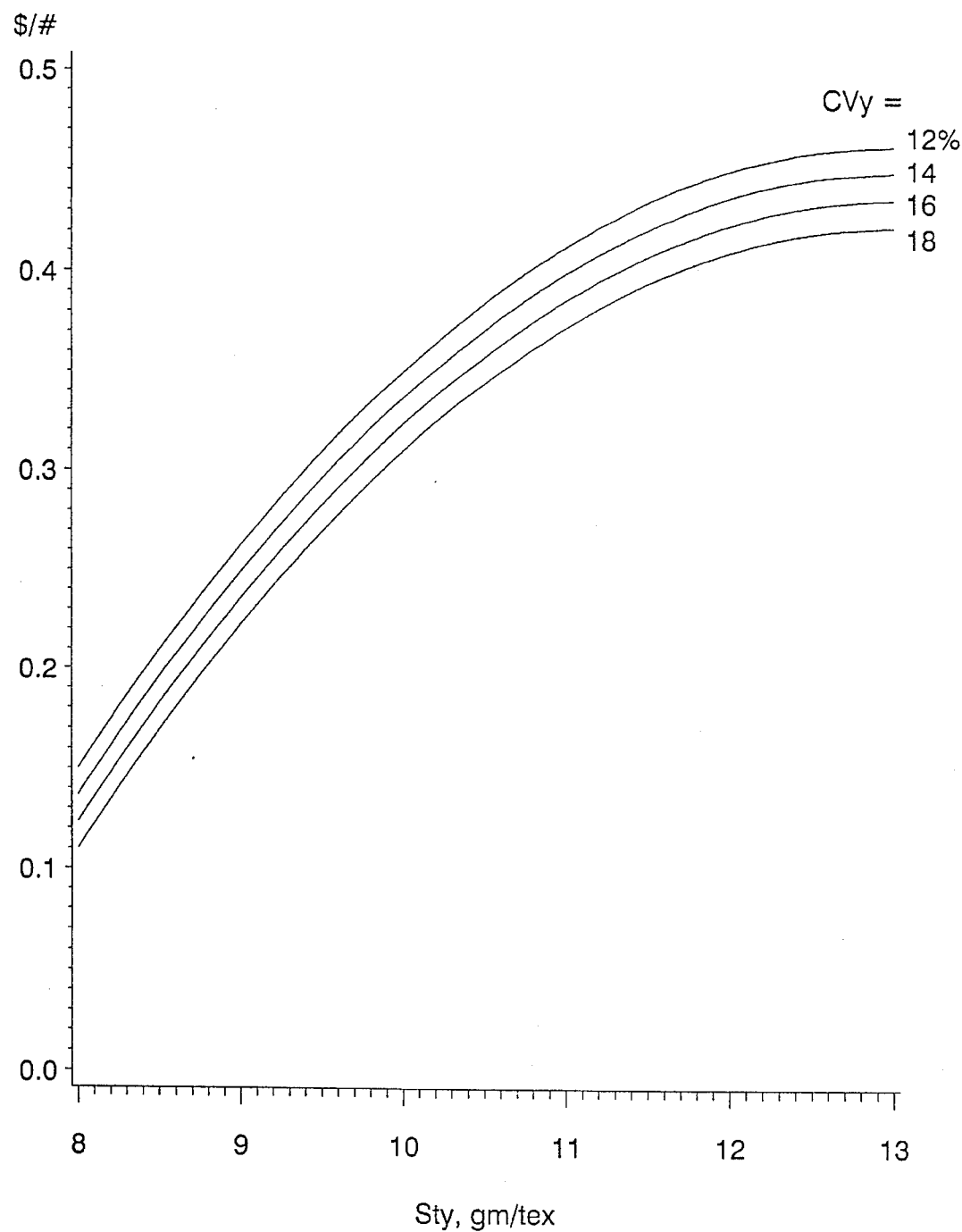
FIGS. 20 and 21 are graphs showing yarn gross profit per pound as a parametric function of yarn parameters.
Figure 21:
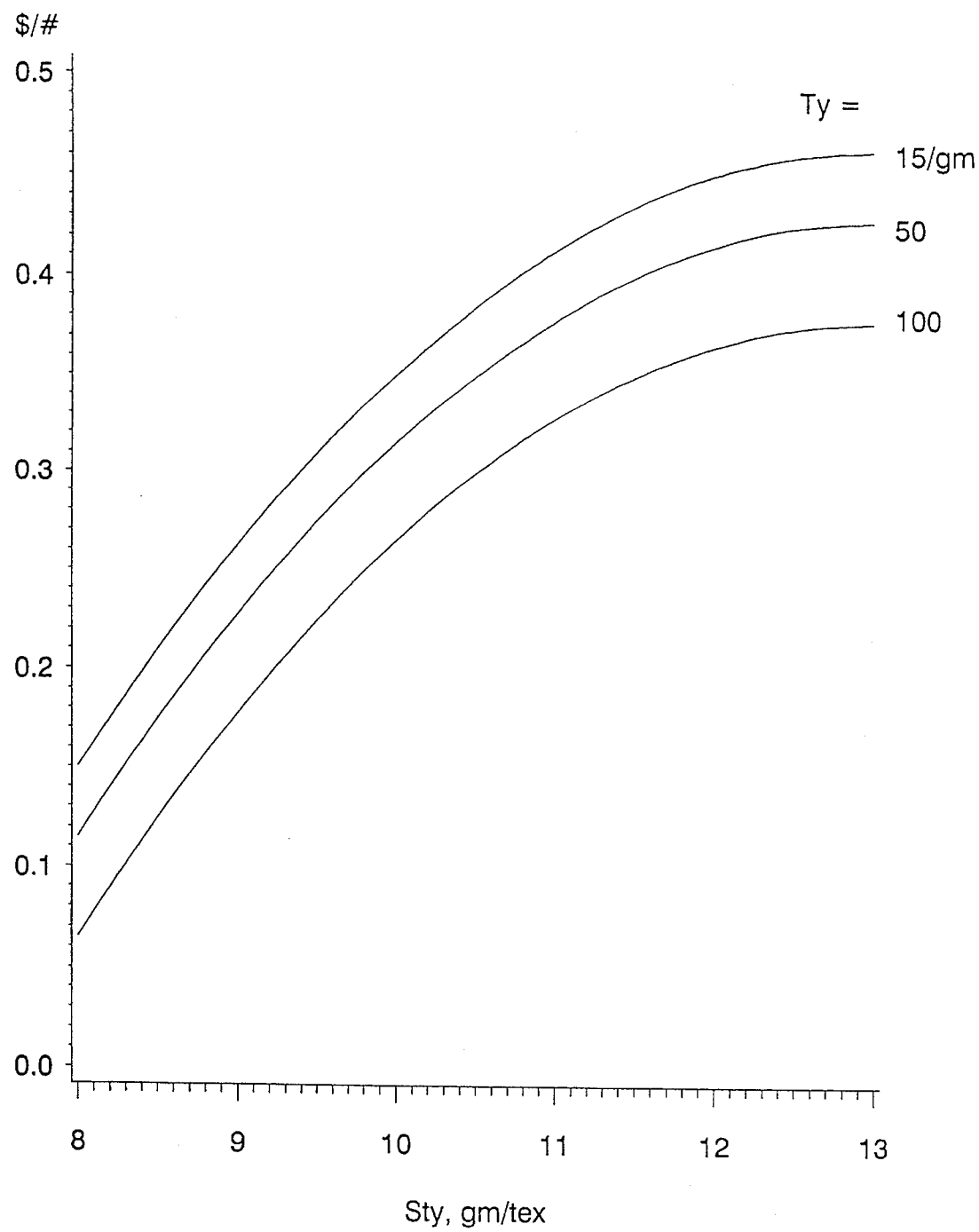

Significant benefit can be realized from modelling the unknown machine or profit characteristics relative to a set of target fiber, machinery, and market operating conditions. Such operation corresponds to a vector "point" and we refer to it as a "Target Operating Point" or "TOP". We call so-defined processing and profit characteristics "α-model" and "β-model", respectively. FIGS. 20 and 21 show yarn gross profit per pound as parametric functions of $St_y$, $CV_y$, and $T_y$. These profit characteristics have similar graphs as the machine characteristics in FIGS. 4 or 5. The explanations for machine characteristics are extended along identical lines to develop a model for gross profit or yarn selling price. Thus, it is sufficient to explain our "α-model" only. Incidentally, FIGS. 20 and 21 are derived from the appropriate terms of the P Equation in FIG. 27 wherein yarn properties are independent variables. These data reasonably reflect market experience.

For each output fiber or yarn property $Y_k$, an α-model structure is assumed, relative to a target operating point for that property, $Y_k^o$ according to $$Y_k = Y_k^o(1+\alpha_k). \tag{12}$$

In this equation, $\alpha_k$ is one component of a vector-valued function which is to be determined according to our methods and which depends upon the deviations from target operating conditions for machine settings, $X^o$, and input fiber properties, $F^o$ $$\alpha = \alpha(X-X^o, F-F^o) = \alpha(\Delta X, \Delta F) \tag{13}$$

Here, X and F are the machine settings and input fiber properties of interest, and ΔX and ΔF are the deviations from target values.

This α-model predicts the behavior of the machine at any machine operating conditions and input fiber properties within the calibration range. Thus the vector function α, once it has been found, can be used in conjunction with equations from the β-model which predict profit or selling price as a function of, among other measurable or predictable factors, output fiber or yarn properties and internal cost accounting data. This fact allows optimal operating conditions to be achieved.

The α-functions have 5 noteworthy features.

a. From the form of Equations 12 and 13, it is evident that the value of $\alpha_k$ expresses the fractional deviation of the output fiber or yarn property $Y_k$ from its target value $Y_k^o$ that is, the coefficients of α are a measure of sensitivity. For example, if $Y_k$ is yarn trash content, then the value of $100 \times \alpha_k$ ($X-X_o$, $F-F_o$) is the predicted percentage by which yarn trash content will differ from its target value when the machine is operated with machine settings specified by the machine vector ΔX and processes input fiber characterized by the property vector ΔF, as both deviate away from the target operating point (TOP).

b. It is also evident that the vector function α is zero in all components if operation is at a TOP.

c. The values of α are therefore a novel and effective vehicle for communicating process performance information to operators, supervisors, management, and computational equipment. Further, the structure of Equations 12 and 13 and the vector function α enables a direct linkage for the model of machine characteristics, and all that implies, to standard and widely accepted tools of statistical process control (SPC).

d. The vector function α can be used to automatically adjust machine settings and/or input fiber properties, or to recommend such adjustments, in a manner which achieves optimal operation of the process. That is, the scalar components of α are the "error signals" in conventional control technology.

e. The vector function α is well suited for extension to other machines and to optimization around their TOPS. Most importantly, our method of model formulation and data acquisition, which determines the model elements, is uniquely and ideally suited to optimize the entire manufacturing process. The α-Model derives much of its suitability from the functional composition described above.

Given a model of profit, which we defined above as the β-model, and the o-model for the manufacturing process, the optimal control problem is seen to have two broad steps: (1) Calibration and (2) Operation. These steps will be explained by detailed example for the α-model and then, in summary, by procedural steps and a logic flow chart. In the second step, target operating conditions, in the sense that profit is maximized, are selected and the machine is operated in the vicinity of the target operating point, TOP. The TOP is selected by maximization of profit, subject to satisfying the constraints on Equation 12 that N, Q, $T_f$, and $SF_f$ be within acceptable limits or "regions of compromise". The control system then periodically or continuously adjusts machine settings and/or selection of input fiber bales with desirable properties. These properties and settings are adjusted in response to measurements of input fiber properties, machine settings, and output fiber or yarn properties in a manner which maintains the values of the components of β and α near zero.

Thus a major innovation of our method is the description of processing and profit characteristics around or near target operating points, TOPs, by experimental procedures executed according to the flow chart described later.

We note that describing process or profit characteristics near TOPs does not necessarily mean that we are restricted to small signal, linear systems techniques. The α- and β-models are general and usually nonlinear.

We now briefly define the β-Model. A profit characteristic is desired which can be used to predict expected profit from values for input fiber properties, machine settings, output fiber or yarn properties, and possibly other factors. For all of the reasons which were cited as benefits for the α-model of the process characteristics, an analogous approach is taken to describe the profit characteristics as $$P = P^o[1+\beta(\Delta X_1, \Delta Y)] \tag{14}$$

where $P^o$ is the target profit, ΔX and ΔF are as before, and ΔY is the deviation of output yarn properties from target values.

D. Specific Example of the α-Model

Since the processing machinery characteristics are generally unknown, the relationships described by Equation 12 must be determined through analysis of measurement data. Many standard and well-known methods exist for determination of functions which describes expected behaviors from a collection of measurements through minimization of a suitably defined error criterion. However, as discussed above, these prior art methods lead to information overload, disguise important interrelationships, even for a single machine, and are less suitable for statistical process control or for automatic, optimal control. For the purpose of explaining our method, one preferred procedure for determination of a vector function α will be described. This will be done using the machine characteristic M for the rotor "spin-box" machine described previously.

Constraints upon the range of fiber properties and machinery operation are first chosen. Consistent with FIGS. 6A to 21, these are:

$$5000 < N < 9500$$
$$1 < Q < 4$$
$$50 < T_f < 250/g$$
$$7 < SF_f < 19\%. \quad (15)$$

We will assume, for simplicity, discrete values for $T_f$ and $SF_f$ $$T_f = 50, 150, 250 \text{ particles/gram and}$$
$$SF_f = 7, 13, 19\% \text{ by weight} \quad (16)$$

We will also assume discrete values for the materials cost advantages resulting from purchase of less expensive materials having the discrete higher trash and short fiber content. These cost advantages are reflected in the gross profit ($/#) results graphed in FIGS. 6A–14D.

CALIBRATION.

Within these regions of operation, multiple values of Q, N, $T_f$, and $SF_f$, are chosen, and "real world", that is "noisy", characteristics are evaluated. For each evaluation, the values of Q, N, $T_f$, $SF_f$, $T_y$, $S_y$, and $CV_y$ are corrupted with random measurement error or noise. This produces a table of synthesized measurements similar to real-world measurements so that we can demonstrate that our method works satisfactorily in the presence of highly variable measurements of fiber and yarn properties. For our purposes here we model the random measurement errors as additive, Gaussian, zero mean, and independent between pairs of measurements. This noise model can be expressed as, for examples, $$Y_m = Y + n_y$$
$$F_m = F + n_f \quad (17)$$

where the subscript "m" denotes a measured value, the vectors "n" denote noise, and the subscripts "y" and "f" are used to denote noise in the measurements of the corresponding variables. This additive noise model simplifies the mathematics and computations involved in determination of the functional relationship α; however, more general noise models can be used, and the functional relationship α can still be found. Thus, the noise model used herein is presented for convenience and is not a limitation of the applicability of the method.

OPERATION.

An initial operating point reference is chosen for machine settings ($N^0$, $Q^0$), input fiber properties ($T_f^0$, $SF_f^0$), and output fiber properties ($T_y^0$, $S_y^0$, $CV_y^0$). These values are used as an initial operating point in the α model; thus, α is zero when the target output fiber or yarn properties are achieved. We choose $N^0 = 7250$ RPM, $Q^0 = 2.5$ CFM $T_f = 150/g$, and $SF_f = 13\%$, for illustration.

The components of the function α, $α_k$, are assumed to have the form $$\alpha_k = \sum_{j=1}^{n} c_j q_j (\Delta N, \Delta Q, \Delta T_f, \Delta SF_f) \quad (18)$$
$$= C_1 + C_2 \Delta N + C_3 \Delta Q + C_4 \Delta T_f + C_5 \Delta SF_f +$$
$$C_6 \Delta N^2 + C_7 \Delta Q^2 + C_8 \Delta T_f^2 +$$
$$C_{10} \Delta N \cdot \Delta Q + C_{11} \Delta N \cdot \Delta T_f + C_{12} \Delta N \cdot \Delta SF_f +$$
$$C_{13} \Delta Q \cdot \Delta T_f + C_{14} \Delta Q \cdot \Delta SF_f + C_{15} \Delta T_f \cdot \Delta SF_f +$$
$$C_{16} N^3 + \ldots$$

where qj = Power series function $$\Delta N = N - N^0$$
$$\Delta Q = Q - Q^0$$
$$\Delta T_f = T_f - T_f^0$$
$$\Delta SF_f = SF_f - SF^0 \quad (19)$$

This form for $\alpha_k$ is equivalent to a multiple variable Taylor's series expansion of $\alpha_k$ around the target operating point.

At this point the coefficients $C_j$ must be determined. This can be formulated in a variety of ways, accounting in various fashions for measurement noise statistics. The simplest and most commonly used is a least squares approach and standard software packages exist which solve this problem, among them SAS, which is used here. (SAS=Statistical Analysis Systems, Inc., Carey, N.C.)

FIG. 28 contains a listing of the various input, output and machinery characteristics, and α-Model elements derived from Equation Set 2 for M without and with measurement noise. We added 10% noise to the fiber measurements, 5% noise to the yarn measurements, and 0% noise to the measurements of machinery settings. Listed below is one element of the vector function for yarn trash content. The coefficients are seen in FIG. 28 (as are those for $\alpha_s$ and $\alpha_c$).

$$\alpha = 50.210464 - 0.000247 \Delta N - 0.176553 \Delta Q + \quad (20)$$
$$0.005694 \Delta T_f + 0.003107 \Delta SF_f + 0 \text{ A } N^2 +$$
$$0.031774 \Delta Q^2 - 0.000007 \Delta T^2 - 0.000664 \Delta SF_f^2 +$$
$$0.000050 \Delta N \cdot \Delta Q - 0.000001 \Delta N \cdot \Delta T_f -$$
$$.000001 \Delta N \cdot \Delta SF_f - 0.001163 \Delta Q \cdot \Delta T_f -$$
$$.000388 \Delta Q \cdot \Delta SF_f + 0.000021 \Delta T_f \cdot \Delta SF_f$$

Equation 20 thus demonstrates the form of the α-model, with noise, to second order.

It is difficult to see if the ever present and large random errors or noise affect the model's predictions by comparison of the $C_j$ in FIG. 27 without and with noise. FIG. 29 gives a partial listing of differences between the process characteristics M and the second order α-model with noise. (In some disciplines, the equations M are called a "truth" model.) For $ST_y$ and $CV_y$, the differences are small. For $T_y$, the differences are larger; the larger differences result from the larger range of $T_f$ and $T_y$ encountered. Evidently, the α-model approximates M satisfactorily, with or without noise.

Both FIG. 28 and FIG. 29 result from one execution of the calculations. The $C_j$ in FIG. 28 with noise and the differences in FIG. 29 will be different for any other execution as a consequence of the real world noise. However, the conclusion that the α-Model well approximates the M-Model is not altered.

FIG. 30 provides coefficients of determination $R^2$ between the machinery characteristics M and the α-Model, even with very large noise effects. This more generally demonstrates that our α-Model approximates M satisfactorily. Indeed, such practical demonstrations of results, as shown in FIGS. 28, 29 and 30, can be extended to more vigorously prove the degree of validity and to further demonstrate the utility of our methods based on α- and β-Models.

The above disclosure demonstrates the validity of our method. We now conclude by demonstrating the utility of our method.

D. OPERATIONAL UTILITY OF THE α AND β MODELS: OPTIMALLY CONTROLLING THE ROTOR SPINBOX

The practical motivation for determining functional relationships α and β is to determine and maintain optimal process operation. Preferably, automatic control means will maintain process operation in the vicinity of optimal TOPS through periodic or continuous adjustment of machine settings and/or input fiber properties. We now describe, in brief overview, how our α- and β model methods facilitate optimal control.

FIG. 31 shows contours for maximum gross profit with spinbox input fiber parameters Tp=150 trash particles/gm and short fiber content $SF_f$=13%. According to the α-Model, with heavy noise contamination, maximum gross profit is 44¢/#, which occurs at machine settings N=6900 RPM and Q=4.0CFM. (See the $ symbol.) Using the machinery characteristics M of FIG. 27, without noise, produces a similar result, 46¢/# at N=7300 RPM and Q=4.0 CFM. The α-Model predictions of yarn parameters $T_y$, $ST_y$, and $CV_y$ are in excellent agreement with the noiseless, exact machinery characteristics M. This constitutes another demonstration that the α-Model works satisfactorily.

Noting in FIG. 31 the yarn properties for most profitable operation of the process with the fiber input fiber $T_y$=43.8, $ST_y$=10.8, and $CV_y$=15, Table 8 gives α- and β-Model results for which the yarn properties are better than 5% below or above the optimum; that is, $T_y \leq 1.05 \times 43.8 = 46.0$, $ST_y \geq 0.95 \times 10.8 = 10.3$, and, $CV_y \leq 1.05 \times 15.0 = 15.8$. The roughly triangular region extending up and to the right from the $ symbol represents a "region of compromise" resulting from the "±5%" constraints. Although the yarn parameters are within ±5% of optimum for all symbols 7, gross profit is always less than the optimum 44¢/#. The lowest gross profit for acceptable yarns ("±5%") is 3.5¢/# below optimum.

FIG. 33 gives contours for this usual business scenario: given opportunities to sell yarn from the process machines, with the yarn being within ±5% of the specification of FIGS. 31 or 32, what is the most profitable input material to the spinbox (not bale state)?

Assuming that the available material has trash range 50<$T_f$<250/gm and 7<$SF_f$<19%, application of the α- and β-Models shows maximum profit to be 52¢/# when buying the most trashy, least-damaged fiber. This is an extremely important example!

FIG. 33 further shows the range of materials which would meet yarn specification but of which, of course, produce less gross profit.

Finally, Table 10 addresses another common and important business scenario: given available input material parameters and an opportunity to sell yarn within ±5% specifications (same as FIGS. 31–33), what is the most gross profit that can be made and what are the machinery settings therefore?

Interestingly, the most and the least gross profit are associated with the 250/gm input. The most gross profit occurs with $SF_f$=7%, the least with $SF_f$=19%. Again, we see the severity of high short fiber content.

E. Flow Chart for Utilization of the α- and β-Models

Thus, the previous processes denoted by the α- and β-models provide a method by which one may determine the various parameters which influence the optimal control of textile processing machinery. With these models, it is possible to develop textile machine control settings for the optimal performance of a given machine.

Initially, a target operational point must be determined. The condition of the target operating point may be selected by contractual obligation and profit maximization. For example, a contract may specify a specific amount of yarn having a certain minimum strength and trash count requirements. Further characteristics such as the quality of the raw fiber as defined by trash content, short fiber content or individual fiber strength are also determined or may be specified.

Further parameters such as the known or experimentally determined performance of the machine given the machine's control settings and input fiber characteristics are also provided. Then, based upon all of these parameters, the optimal control settings of the machine may be calculated based upon techniques described with respect to the α and β-Models. Finally, the calculated control settings are then made on the machine so that the output product of the machine matches the target operating point.

The control method basically involves two primary steps, developing a model of the machine or machines involved, as was described with respect to the α- and β-Models, by experimental operation of the machine over its full operational range and utilization of target criteria. The model is then used to determine the control settings to achieve the target criteria. Thus, using the disclosed method provides optimal control of the machine without the wasted time and unprofitability associated with trial and error determination of control settings or the inflexible use of preset control settings.

Figure 22:
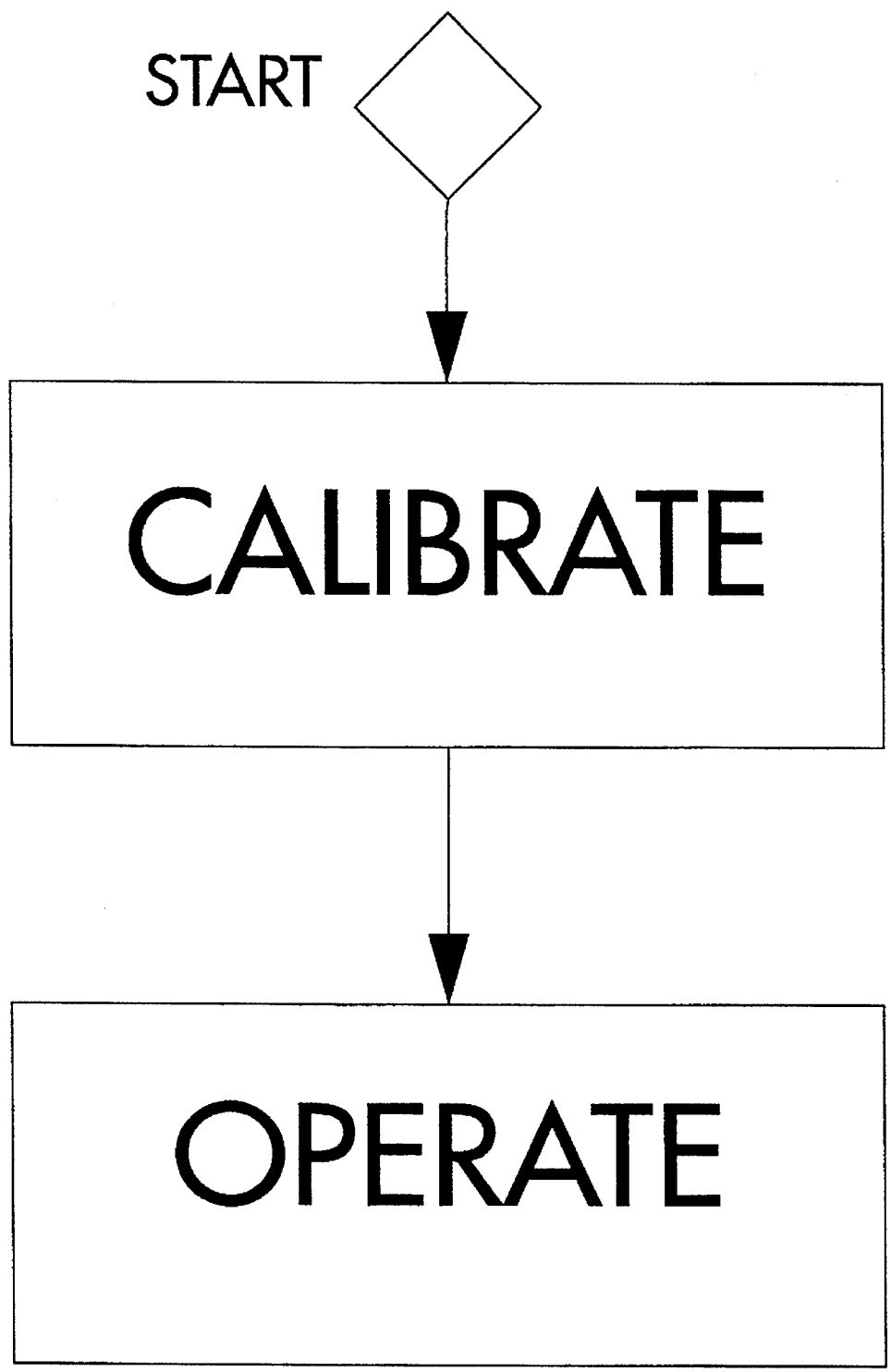
FIG. 22 is schematic diagram of the calibration of the model.

The two primary steps are represented in the flow chart of FIG. 22 as the calibration and operate steps. The calibration step corresponds to the step of developing the models and determining the optimal control settings and input characteristics as described. The operate step corresponds to operation of the machine in accordance with determined input material characteristics and control settings.

Figure 23:
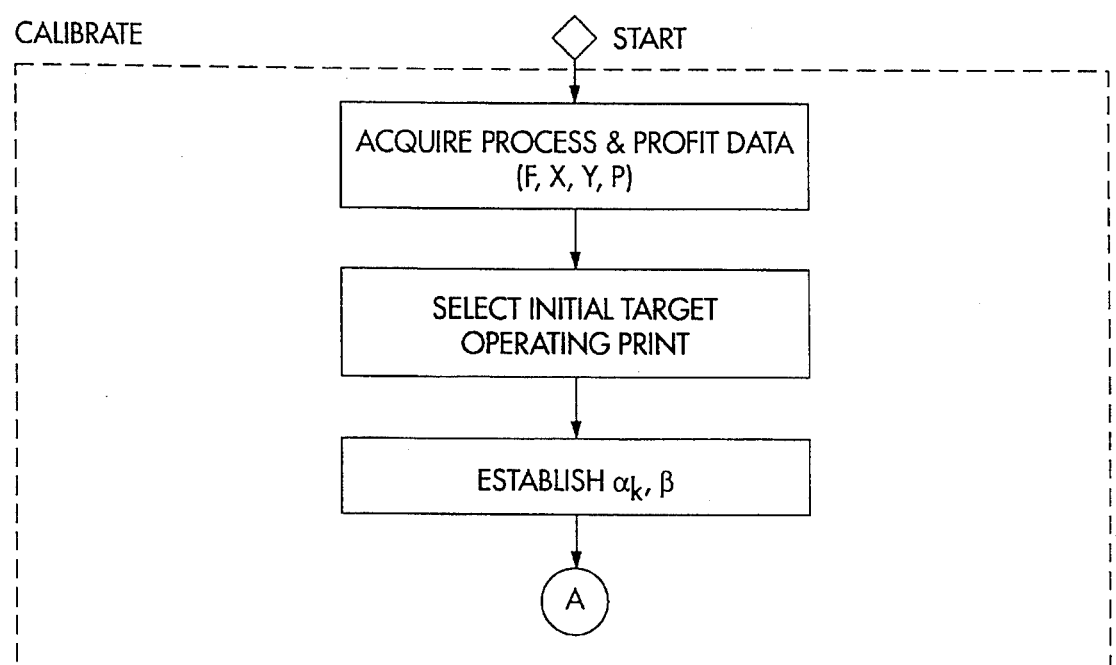
FIG. 23 is an expanded version of the flow chart of FIG. 22.
Figure 24:
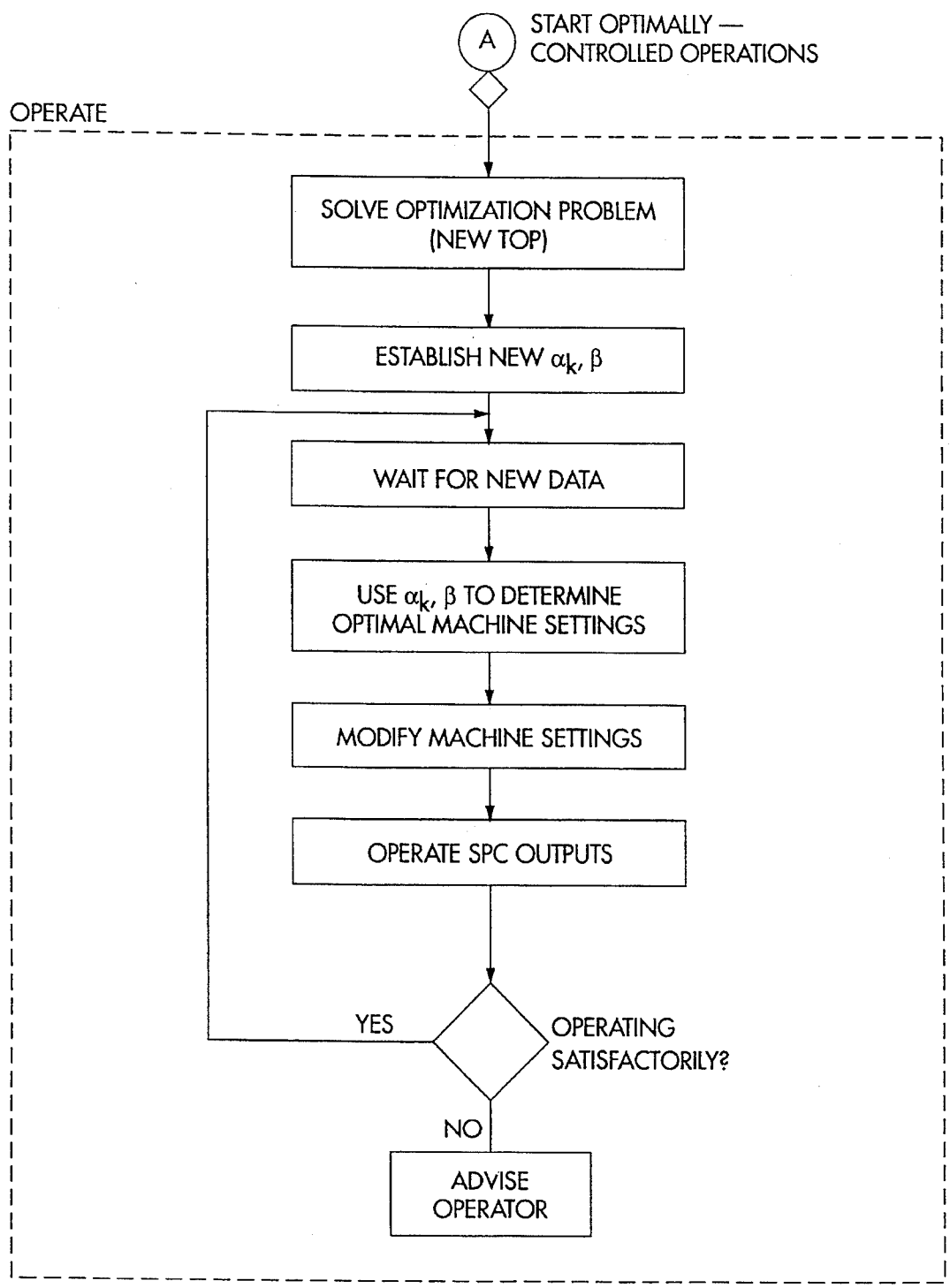
FIG. 24 is a further expansion of the flow charts of FIGS. 22 and 23.

The flow chart of FIG. 23 is an expanded version of that of FIG. 22. As expanded, the calibration step includes the sub-steps of acquiring process and profit data, selecting the target operating point and establishing the α- and β-Models in accordance with the data. The operate step then comprises the sub-steps of operating the machine under the determined optimal conditions, and the further step of generating operational corrections based on errors. The step of generating operational corrections is accomplished by monitoring the output of the machine for conformance with the target operating point, establishing new α-and β-Models based on the new data using the corrected α- and β-Models to determine the proper input parameters and machine settings, adjusting the machine and operation. As the flow chart indicates, the process of developing the correct models and resulting control conditions may be ongoing to allow for the fine tuning of the operation of the machine to achieve greater conformance to the target operating conditions.

While the preferred method has been described with respect to a preferred embodiment in a yarn spinning setting, it can easily be adapted to any step of the textile processing art from ginning of cotton to production of cloth. The adaptation to these various processes would simply entail the use of a new set of variables specific to each type of machinery used and may be performed without departing from the scope of the claims as set forth below.

What is claimed is:

1. A method for optimally processing fiber wherein the method is carried out in a machine having inputs and an output, said method comprising the steps of:

determining a machinery model which simulates the operation of a fiber processing machine given a range of input parameters at least at a first time by:
  a. measuring fiber processing machinery characteristics over ranges of operational settings, said characteristics defining the interrelationships between input fiber parameters and output fiber or yarn parameters over said ranges of machinery settings;
  b. defining a machine model from said machinery characteristics;

measuring fiber parameters at the inputs to said fiber processing machines at least at a second, later time;

introducing said input fiber parameters into said model and then determining machinery settings, within a predetermined range of acceptable variation, which settings optimize at least one output parameter, including profit;

adjusting said machinery settings in accordance with the determination of machinery settings to optimize at least one output parameter; and processing fibers with said optimally adjusted machinery.

2. A method for optimally processing fiber wherein said method is carried out in a plurality of sequentially related fiber processing machines each of which having input and output, said method comprising the steps of:

determining a machinery model which simulates the operation of a fiber processing machine given a range of input parameters at least at a first time by:
  a. measuring fiber processing machinery characteristics over ranges of operational settings for each of said machines, said characteristics defining the interrelationships between input fiber parameters and output fiber or yarn parameters over said ranges of machinery settings; and
  b. defining a machine model for each of said machines from said machinery characteristics;

measuring fiber parameters at the inputs to said fiber processing machines at least at a second, later time;

introducing said input fiber parameters into a composite machinery model and then determining settings for each machine, within a predetermined range of acceptable variation;

adjusting said machinery settings in accordance with the determination of machinery settings for each of said machines to optimize at least one output parameter; and processing fibers with said optimally adjusted machines.

3. A method for inputing raw fiber materials having optimal parameters into textile processing machinery to achieve an output of textile material corresponding to a target operating point, comprising the steps of:

determining a machinery model which simulates the operation of a fiber processing machine given a range of input parameters by:
  a. measuring fiber processing machinery characteristics over ranges of operational settings, said characteristics defining the interrelationships between input fiber parameters and output fiber or yarn parameters over said ranges of machinery settings; and
  b. defining a machine model from said machinery characteristics;

determining characteristics of a desired output fiber or yarn parameters or profit;

introducing said output fiber or yarn parameters into said machinery model which determines the optimum range of input fiber parameters;

selecting input fiber having parameters coinciding with the determined optimum range of input fiber parameters;

providing said selected input fibers as input to a fiber processing machine; and operating the textile machinery with selected input fibers to produce the output corresponding to the target operating point.

4. A method for optimally processing input material wherein the method is carried out in textile processing machinery to achieve an output corresponding to a target operating point from a range of available input material and machinery control settings comprising the steps of:

providing a range of input material corresponding to the available range of such input material, the range of material including a substantially complete sample of the various qualities and grades of input material available;

operating the machinery over the entire range of provided input material to generate output material;

varying the control settings of the machine over their full range while operating the machinery over the range of input material to generate the output material such that substantially all combinations of input material and control settings are used to generate output material;

testing the output material to determine various characteristics of the output material at substantially all combinations of input material and control settings;

generating a database of substantially all combinations of input material characteristics, machinery control settings and output material characteristics;

selecting a target operating point including at least one parameter selected from a group comprising the input material characteristics, the machinery settings or the output material characteristics;

defining a model of machinery performance based upon a selected portion of the database which is within a predetermined region of the target operating point;

using the model for determining at least one optimal parameter from the group comprised of the optimal input material characteristics, the optimal machinery control settings, or the optimal output material characteristics; and operating the machinery to process input material to produce output material in accordance with the optimal parameter.

5. The method of claim 4 wherein at least one optimal parameter comprises optimal machinery control settings and an optimal input material characteristic and further comprising selecting input material having optimal input material characteristics for input to the machinery and adjusting the machinery to operate at the optimal machine control settings.

6. The method of claim 5 further comprising the steps of:

testing the output material produced by the machine after it has operated with the determined optimal input material characteristics and optimal control settings to determine its correspondence to the target operating point criteria;

calculating the amount of error between output material produced and the target operating point criteria;

adjusting the calculated model of machinery performance in accordance with the calculated error;

re-determining the optimal input material characteristics and machinery control settings;

selecting input material having characteristics corresponding to the re-determined optimal characteristics for input to the machinery;

adjusting the machinery control settings to correspond to the re-determined optimal machinery control settings; and operating the machinery at the re-determined optimal control settings and with the input material having the re-determined input material characteristics to produce output material corresponding to the target operating point criteria.

7. The method of claim 5 wherein the input material is staple fibers, the output material is yarn and the machinery is yarn spinning machinery.

8. The method of claim 5 wherein the input material is yarn, the output material is cloth and the machinery is weaving machinery.

9. The method of claim 5 wherein the input material is staple fibers, the output material cloth and the machinery comprises yarn spinning machinery and weaving machinery.

10. The method of claim 5 wherein the selected target operating point criteria comprise at least one of, output material profit margin, output material short fiber content, output material trash content, output material tensile strength, output material color and output material dyeability.

11. The method of claim 5 wherein the input material characteristics comprise at least one of, input material cost, input material short fiber content, input material trash content, input material tensile strength, input material color, and input material maturity.

12. The method of claim 5 wherein the machinery comprises yarn spinning machinery, the input material is staple fiber and the output material is yarn and the machinery control settings comprise at least one of a trash extracting flow rate in the opening/cleaning stage of the spinning machine or an opening cylinder speed of the opening cylinder of the opening/cleaning stage of the spinning machine.

13. A method for optimally processing input material wherein the method is carried out in textile processing machinery to achieve an output corresponding to a target operating point from a range of available input material and machinery control settings comprising the steps of:

providing a range of input material corresponding to the available range of such input material, the range of material including a substantially complete sample of the various qualities and grades of input material available;

operating the machinery over the entire range of provided input material to generate output material;

varying the control settings of the machine over their full range while operating the machinery over the range of input material to generate the output material such that substantially all possible combinations of input material and control settings are used to generate output material;

testing the output material to determine various characteristics of the output material;

generating a first database of the various input material characteristics, machinery control settings and output material characteristics;

providing a second database of profit data;

providing first and second target operating points based upon at least one of the following: input material characteristics, machinery control settings, output material characteristics, and profit data;

defining an first model of machinery performance based upon the first database within a predetermined range of the first target operating point;

defining a second model of profit based upon the second database within a predetermined range of the second target operating point;

using the first model and the second model determining the optimal input material characteristics and machinery control settings to provide an output material meeting the criteria of the first and second target operating points;

selecting input material having the characteristics meeting the determined optimal characteristics for input to the machinery;

adjusting the machinery control settings to correspond to those determined to be optimal;

operating the machinery at the optimal machinery control settings to process the selected optimal input material and to produce output material corresponding to the criteria of the target operating point; and testing the output material produced by the machine after it has operated with the determined optimal input material characteristics and optimal control settings to determine its correspondence to the target operating point criteria.

14. The method of claim 13 further comprising:

calculating the amount of error between output material produced and the first target operating point;

adjusting the calculated $\alpha$-model of machinery performance in accordance with the calculated error;

re-determining the optimal input material characteristics and machinery control settings;

selecting input material having characteristics corresponding to the re-determined optimal characteristics for input to the machinery;

adjusting the machinery control settings to correspond to the re-determined optimal machinery control settings; and operating the machinery at the re-determined optimal control settings and with the re-determined input material characteristics and to produce output material corresponding to the target operating point criteria.

15. The method of claim 13 wherein the input material characteristics comprise at least one of, input material cost, input material short fiber content, input material trash content, input material tensile strength, input material color, and input material maturity.

16. The method of claim 13 wherein the machinery comprises yarn spinning machinery, the input material is staple fiber and the output material is yarn and the machinery control settings comprise at least one of a trash extracting flow rate in the opening/cleaning stage of the spinning machine or an opening cylinder speed of the opening cylinder of the opening/cleaning stage of the spinning machine.

* * * * *

UNITED STATES PATENT AND TRADEMARK OFFICE
CERTIFICATE OF CORRECTION

PATENT NO. : 5,560,194
DATED : October 1, 1996
INVENTOR(S) : Frederick M. Shoffner, et. al It is certified that error appears in the above-indentified patent and that said Letters Patent is hereby corrected as shown below:

Column 4, line 18, after "could" delete "he" and insert -- be --.

Column 14, line 17, delete "o-model" and insert -- α-model --.

Column 16, line 53, after "FIG." delete "27" and insert -- 28 --.

Column 17, line 40, delete "Table 8" and insert -- FIG. 32 --.

Signed and Sealed this

Twenty-fourth Day of December, 1996

Attest:

BRUCE LEHMAN

*Attesting Officer*   *Commissioner of Patents and Trademarks*